(12) United States Patent
Turki et al.

(10) Patent No.: US 11,725,219 B2
(45) Date of Patent: *Aug. 15, 2023

(54) **BIOFIXATION OF GREENHOUSE GAS BY MASS CULTURE OF *HAEMATOCOCCUS* SP. *KAU-01* MICROALGA IN HIGH EFFICIENCY MEDIUM**

(71) Applicant: King Abdulaziz University, Jeddah (SA)

(72) Inventors: Adnan Jaman Turki, Jeddah (SA); Md. Abu Affan, Jeddah (SA); Salim Marzoog Al-Harbi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 32 days.

This patent is subject to a terminal disclaimer.

(21) Appl. No.: 17/113,816

(22) Filed: Dec. 7, 2020

(65) Prior Publication Data

US 2022/0177929 A1 Jun. 9, 2022

(51) Int. Cl.
| | | |
|---|---|---|
| *C12N 1/12* | (2006.01) | |
| *C12P 5/02* | (2006.01) | |
| *C12N 1/20* | (2006.01) | |
| *C12R 1/21* | (2006.01) | |

(52) U.S. Cl.
CPC ............... *C12P 5/023* (2013.01); *C12N 1/20* (2013.01); *C12N 1/205* (2021.05); *C12R 2001/21* (2021.05)

(58) Field of Classification Search
CPC ................................ C12N 1/12; C12N 5/0018
See application file for complete search history.

(56) References Cited

U.S. PATENT DOCUMENTS

| 11,326,186 B1 * | 5/2022 | Turki ...................... C12N 1/12 |
| 2020/0232003 A1 * | 7/2020 | Kuehnle ................. A61Q 19/00 |
| 2022/0177929 A1 * | 6/2022 | Turki ...................... C12N 1/12 |

FOREIGN PATENT DOCUMENTS

| CN | 101849505 B | 7/2012 | |
| CN | 106479898 A | 3/2017 | |
| JP | 8-89279 A | 4/1996 | |
| KR | 10-1298944 B1 | 8/2013 | |
| WO | WO 2014/142540 A1 | 9/2014 | |
| WO | WO-2014142423 A1 * | 9/2014 | ............... C12P 1/00 |

OTHER PUBLICATIONS

Goksan et al., "Growth characteristics of the alga *Haematococcus pluvialis* Flotow as affected by nitrogen source, vitamin, light and aeration", Turkish Journal of Fisheries and Aquatic Sciences, vol. 11, pp. 377-383, 2011 (Year: 2011).*

Cheng et al., "Gradient domestication of Haematococcus pluvialis mutant with 15% CO2 to promote biomass growth and astaxanthin yield", Bioresource Technology, vol. 216, pp. 340-344, 2016 (Year: 2016).*

English machine translation of WO 2014/142423A1, published Sep. 18, 2014 (Year: 2014).*

R. Sarada, et al., "Optimization of culture conditions for growth of the green alga *Haematococcus pluvialis*", World Journal of Microbiology & Biotechnology, vol. 18, 2002, pp. 517-521 (Abstract only).

* cited by examiner

*Primary Examiner* — Tekchand Saidha
(74) *Attorney, Agent, or Firm* — Oblon, McClelland, Maier & Neustadt, L.L.P.

(57) ABSTRACT

The invention is directed to a culture medium for *Haematococcus* that contains combustion gases like carbon dioxide, carbon monoxide, and oxides of nitrogen or sulfur and which fixes the carbon, nitrogen or sulfur in these combustion gases into biomass and to methods providing superior biomass yields using this culture medium to culture select species of *Haematococcus* such as *Haematococcus* sp. KAU-01.

15 Claims, 15 Drawing Sheets

FIG. 8A
FIG. 8B
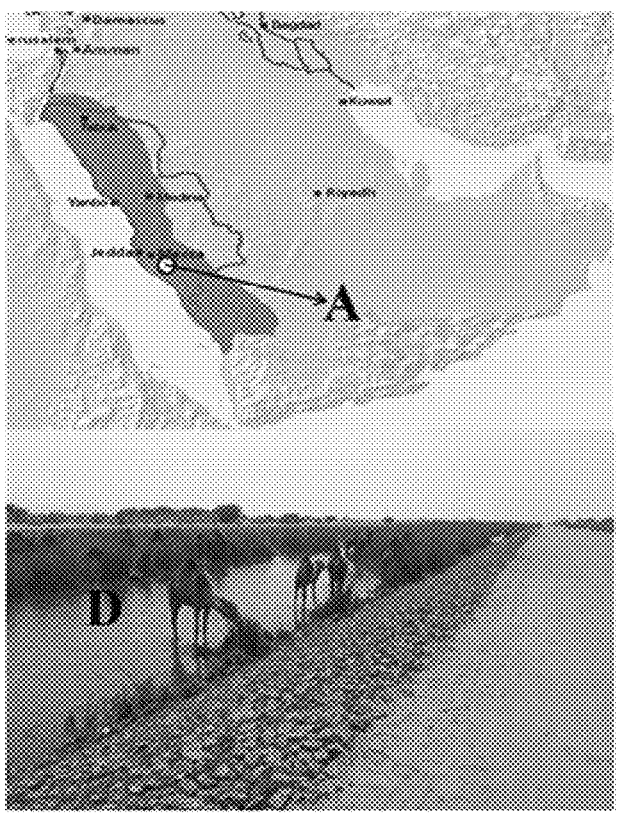
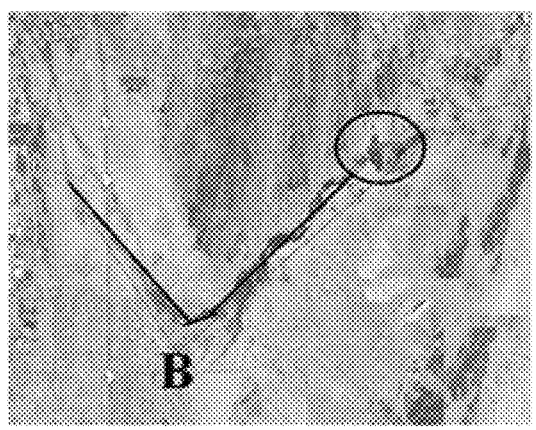
FIG. 8C
FIG. 8D

FIG. 9
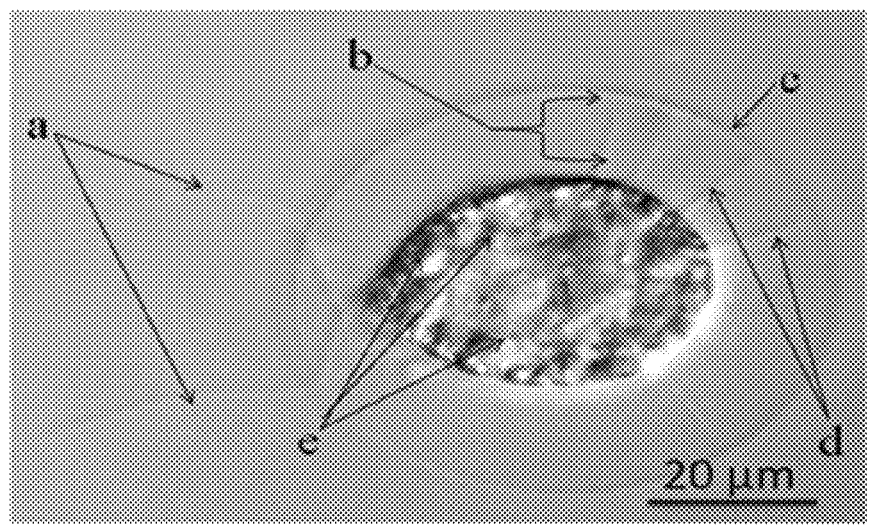
FIG. 10A    FIG. 10B    FIG. 10C
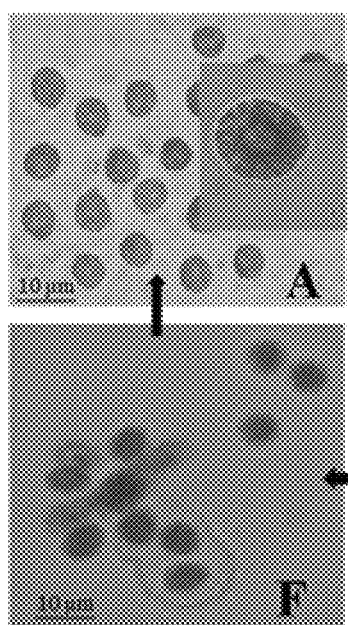 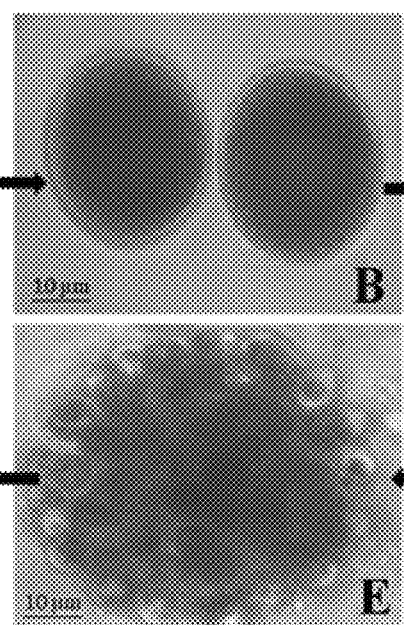 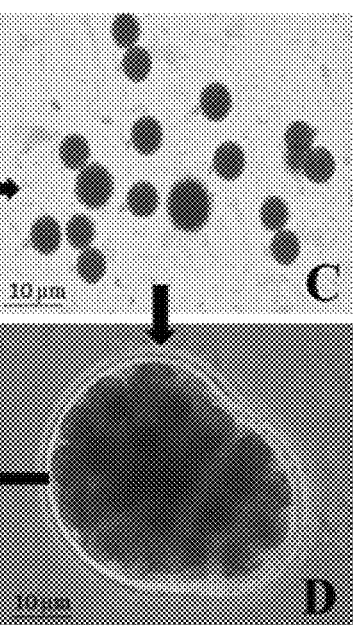
FIG. 10F    FIG. 10E    FIG. 10D

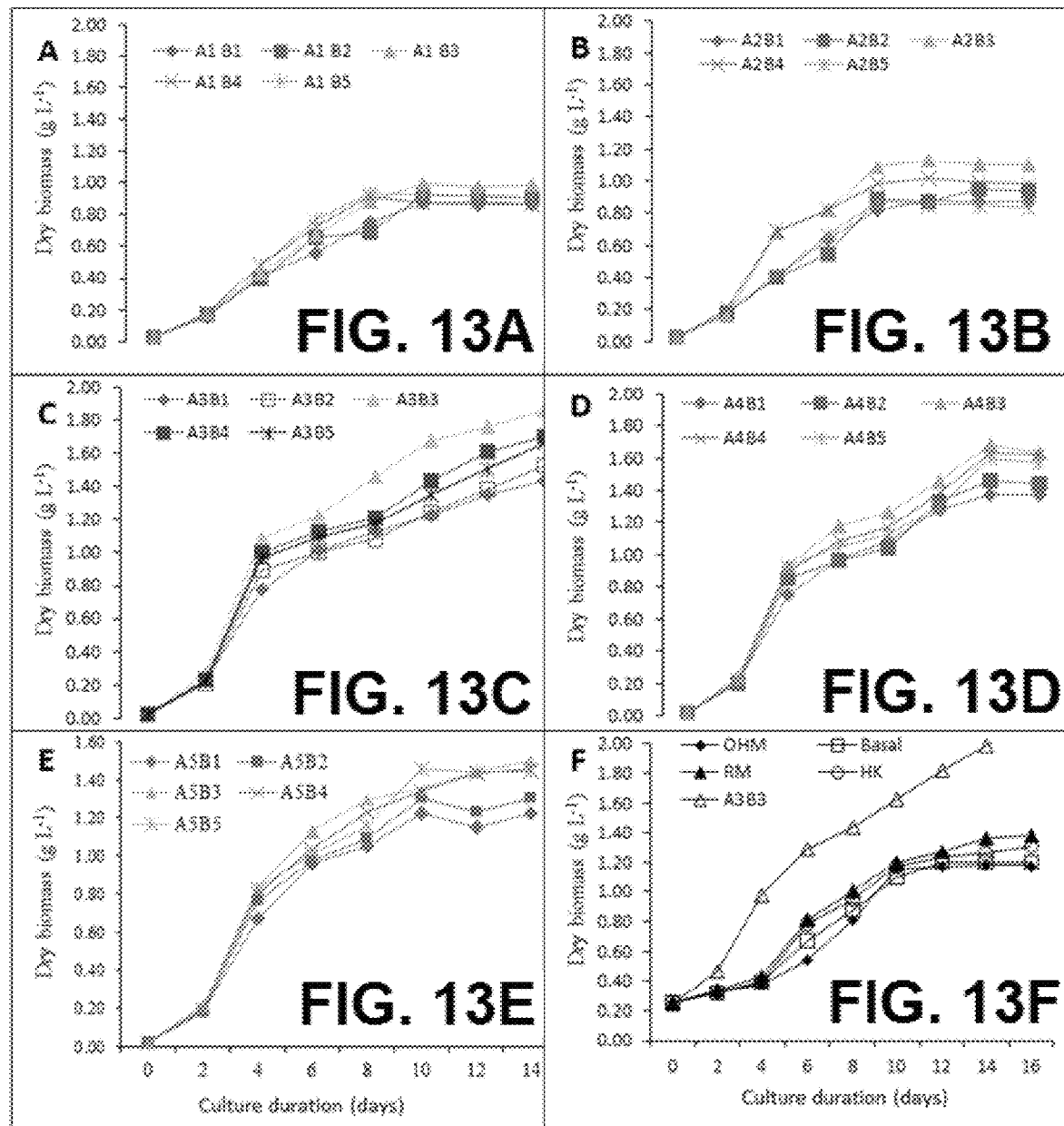

BIOFIXATION OF GREENHOUSE GAS BY MASS CULTURE OF *HAEMATOCOCCUS* SP. *KAU-01* MICROALGA IN HIGH EFFICIENCY MEDIUM

CROSS-REFERENCE TO RELATED APPLICATION

This application is related to U.S. application Ser. No. 17/113,754, filed Dec. 7, 2020, entitled HAEMATOCOCCUS SP. STRAINS AND MEDIUM FOR EFFICIENT BIOMASS PRODUCTION USING GREENHOUSE GASES, which is hereby incorporated by reference.

BACKGROUND

Field of the Invention

The invention pertains to algology and environmental science, especially microalgae culture media and methods that enhance fixation and removal of carbon dioxide and other flue gases produced by fuel combustion such as those produced by coal-fired power plants.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

It is well known that carbon dioxide is an important greenhouse gas ("GHG") which can persist in the atmosphere for a long time. Carbon dioxide concentrations in air are increasing due to combustion of coal, petroleum, natural gas, and other fuels to produce energy. The increased atmospheric concentration of carbon dioxide plays a major role in global climate change, global warming, acid rain, ocean acidification, and other malignant environmental problems. Average planetary surface temperatures correlate with increases in atmospheric carbon dioxide and can lead to alterations in precipitation patterns, rises in sea level, and accelerated glacial melting.

Coal-fired power plants release carbon dioxide and other flue and greenhouse gases into the environment. Biofixation has been proposed as one way to reduce the emissions of gas produced by combustion into the atmosphere. Carbon dioxide and other combustion gases can be used as feedstocks to culture microorganisms such as microalgae that fixing them in organic materials such as biodiesel fuels, animal feeds, aquaculture feeds, and other high-valued materials such as pigments and nutraceutical products including astaxanthin; Cheng, J., et al., *Gradient domestication of Haematococcus pluvialis mutant with 15% $CO_2$ to promote biomass growth and astaxanthin yield*, BIORESOUR. TECHNOL., 2016, 216, 340-344; Williams, P. J. et al., *Microalgae as biodiesel & biomass feedstocks: review & analysis of the biochemistry, energetics & economics*. ENERGY ENVIRON. SCI. 2010, 3: 554-590; and Zheng, Q., et al., *Energy efficient transfer of carbon dioxide from flue gases to microalga systems*. ENERGY ENVIRON. SCI, 2016, 9: 1074-1082. Consequently, it is of critical importance to design and formulate a simple, efficient and inexpensive process for incorporating carbon dioxide and other combustion gases, which are generated from stationary sources like coal-fired power plants, into biomass and simultaneously remove these gases from the environment.

Numerous proposals have been made to attempt to capture and remove carbon dioxide produced by fossil fuel combustion or from the atmosphere. These include using molecular sieves or solvents to physically and chemical absorb carbon dioxide. Other methods include low temperature or cryogenic separation of carbon dioxide from air or other gases. Once carbon dioxide has been captured or separated in has been proposed to transport in and store it in geological formations. However, these methods for capturing and storing carbon dioxide are logistically complicated and expensive. Moreover such methods create new environmental risks including groundwater contamination or acidification, or geological instability including earthquakes. Such methods also create a new risk of leakage of the chemically or physically captured or separated carbon dioxide back into the atmosphere. Physical or chemical adsorption or separation and storage of carbon dioxide also do not solve problems associated with other gaseous components of combustion gas mixtures such as CO, $NO_x$ and $SO_x$.

In view of the above, the biological capture and fixation of carbon dioxide and other combustion gases into more complex molecules using microorganisms such as microalgae could offer a simple, convenient and economical way to capture carbon dioxide and other combustion gases. However, significant work is required to identify microalgae strains, culture media, and culture conditions suitable for efficient biofixation of carbon dioxide and other combustion gases. This is because different microalgae strains have different biochemical properties and growth rates and because conventional media limit the rate at which a microorganism can fix carbon dioxide or other combustion gases.

There is a significant need for a way to fix carbon dioxide and other combustion gases into biomass, most preferably, valuable biomass such as natural pigments. However, many conventional strains of microbes which can fix carbon dioxide have slow growth rates or produce little or no biomass of significant value. For example, many strains of the microalgae *Haematococcus* which can produce astaxanthin or other valuable natural pigments have slow growth rates in conventional media. These slow growth rates both limit their ability to remove carbon dioxide and other combustion gases from the air as well as negatively impacting the value of biomass they produce.

In addition to fixing combustion gases into biomass, the microbial production of natural pigments such as astaxanthin could supply a growing commercial market for these compounds which include polyisoprenoids such as β-carotene, astaxanthin, and canthaxanthin. These pigments are receiving greater attention because they are often used in the food, nutrition, and cosmetics industries; Patricia Veiga-Crespoet et al., *Influence of culture conditions of Gordonia jacobaea MV-26 on canthaxanthin production*, INTERNATIONAL MICROBIOLOGY, 2005, 8, 1. These pigments may be used for aquaculture of in animal feeds such as poultry feed or in nutraceuticals. For example, astaxanthin is a derivative of beta-carotene that is used as a food additive and natural colorant to enhance the appearance of pale colored cultured fish and shellfish, such as salmonoid fish and shrimp. It has been reported to have anti-inflammatory, anticancer and immunomodulatory properties and to confer numerous other health benefits for humans.

*Haematococcus* sp. often contain a high cellular content of astaxanthin typically ranging above 4% of its dry weight; Lee, Y. K., et al., *Accumulation of astaxanthin in Haema-* tococcus lacustris (Chlorophyta). JOURNAL OF PHYCOLOGY. 1992, 3003, 575-577; Torzillo et al., JOURNAL OF APPLIED PHYCOLOGY, 2003, 15: 127-136. The cost of the dried powder of Haematococcus sp. is about 500 to $1,500/kg depending on its beta carotenoid and astaxanthin content; the price of purified astaxanthin can range upwards from about $70,000/ kg.

Haematococcus is found world widely and its natural habitats are characterized by their unstable temporary conditions, which occur in small rock pools, water holes, bird baths, and other small natural or artificial bodies of water. Haematococcus sp. are unicellular green microalga with two flagella. They exhibit two types of cell morphology depending on environmental conditions. Under optimal growth conditions the cells are green and vegetative, proliferative, and capable of actively swimming using their flagella. However, under unfavorable conditions, the green vegetative cells drastically increase in volume, cease to be motile, and enter a resting stage to form cyst.

The green vegetative cells of Haematococcus are primarily composed of carotenoids which can contain 75-80 wt. % lutein, 10-20 wt. % β-carotene, as well as violaxanthin, neoxanthin, zeaxanthin, and chlorophyll a and b; Shah, M. M. R., et al., *Astaxanthin-producing green microalga Haematococcus pluvialis: From single cell to high value commercial products*. FRONT. PLANT SCI. 2016, 7, 531.

Typically astaxanthin production from Haematococcus is achieved through a two-stage culture comprising a vegetative (green) stage and aplanospore (red) stage. However, vegetative cultivation of Haematococcus is problematic due to slow growth rates, low cell densities, and susceptibility to contamination. Arrest of the growth of Haematococcus has been attributed to various factors including the production of immotile cells at a pH above 9.0, which can occur when a culture generates significant amounts of ammonia; conversion of vegetative motile cells into cysts after 4-6 days in conventional media; and release of cellular debris and blockade of the Haematococcus outer membrane by the cellular debris. Unfortunately, while Haematococcus sp. can produce valuable biomass they lack the growth rates necessary to efficiently metabolize large quantities of carbon dioxide such as that in combustion or flue gases from coal-fired plants.

While many efforts have been made to boost the production of biomass from microalgae by using different media formulations, different kinds of vitamins, variation of light intensity or by use of mixed cultures of different algae, none have resulted in significant increases in production of algal biomass. Further, while conventional fed-batch microalgae culture can provide nutrients to facilitate continued microalga growth, it does not remove chemical inhibitors of microalga growth, such as free fatty acids like EPA. This results in the cessation of growth of the microalgae cultured followed by its gradual deterioration.

Apart from free fatty acid inhibitors, other culture components can inhibit microalga growth including debris generated from aging cell walls and broken cells. The inventors found that these materials inhibit microalga growth by favoring the formation of large cell aggregates which sequester nutrients needed for active growth of Haematococcus and other microalgae and which diminish the ability of microalgae to adsorb light.

Other factors which impair or inhibit the growth of Haematococcus and the production of valuable biomass include the presence of contaminating microalgae or other microorganisms and sensitivity of microalgae to culture conditions, such as the source, intensity and light provided during cultivation In view of the problems described above, the inventors sought to formulate a culture medium and conditions for cultivation of select Haematococcus microalgae strains that avoid the problems with conventional Haematococcus strains, culture media and culture methods in order to enhance biofixation of combustion gases as well as produce high yields of valuable biomass.

BRIEF SUMMARY OF THE INVENTION

Taking into account problems and limitations of existing culture media and culture methods, the inventors developed a culture medium, Affan-Adnan Haematococcus King Abdulaziz University or "AAHKAU" medium, containing both macro- and micronutrients. They also developed efficient mass culture methods that inhibit the contamination Haematococcus cultures by other microorganisms when tap water is used to prepare the culture medium. The culture methods developed by the inventors also remove inhibitors of microalgae growth. Use of AAHKAU medium in combination with select strains of Haematococcus, such as Haematococcus sp. KAU-01, and the other improvements developed by the inventors provides a simple, economic and efficient way to fix carbon dioxide and other combustion gases into biomass.

Surprisingly, the inventors found that culturing Haematococcus in a specially formulated medium, AAHKAU medium, in the presence of combustion or flue gases that included carbon monoxide and nitrogen oxides in addition to 15% carbon dioxide resulted in superior growth rates and biomass production compared to microalgae grown in the presence of normal air or 15% $CO_2$ alone.

It was also found that periodic replacement of a portion of the culture medium increased growth and biomass production compared to other culture modes.

The inventors found that careful regulation of calcium and magnesium content of the culture medium were important to enhancing biomass production by Haematococcus. The inventors found that culture medium containing no or too little calcium increased lysis of Haematococcus and that low concentrations of magnesium produced weak, pale vegetative cells rather than dark green vegetative cells produced when sufficient magnesium was provided. However, the inventors also observed that culture media with too high a calcium or magnesium concentration became turbid at alkaline pH resulting in arrested growth of Haematococcus. It was found that excess concentrations of Ca or Mg produced undesirable turbidity in the culture. Turbidity creates two types of problems: (a) cell movement and propagation will be stopped and (b) if the culture is not being agitated then nutrients will sediment and floating microalgae in the liquid or supernatant portion of the culture will not get sufficient nutrient for growth.

The inventors discovered that acidifying water used to make Haematococcus mass culture medium to about pH 3.0 prior to its use significantly removed microorganisms which compete or otherwise reduce the growth and biomass production of Haematococcus. Prior to use, the pH of the acidified water is adjusted upward by addition of a base such as $Na_2CO_3$ which can also provide carbon needed for microalgae photosynthesis. This is a valuable step as it is difficult to sterilize the large amounts of water needed for mass culture of Haematococcus.

Furthermore, the inventors found that *Haematococcus* biomass production could be increased by removing inhibitors of microalgae growth and by retaining viable microalgae cells by filtering a *Haematococcus* culture, for example, through a bag net filter having a 4, 5 or 6 μm mesh size, followed by replacement of a portion of the spent medium with fresh medium.

The invention includes, but is not limited to the following embodiments.

A method for producing biomass comprising culturing *Haematococcus* in a culture medium in the presence at least one combustion gas and light, thereby producing biomass; wherein said culture medium comprises, consists essentially or, or consists of from 187.5 to 562.50 mg/L $NaNO_3$, 37.50 to 112.50 mg/L $KNO_3$, 12.50 to 37.50 mg/L $Ca(NO_3)_2$, 27.50 to 82.50 mg/L $Mg(NO_3)_2 \cdot 6H_2O$, 22.50 to 67.50 mg/L $K_2HPO_4$, 20.00 to 60.00 mg/L $KH_2PO_4$, 5.00 to 15.00 mg/L $K_2SO_4$, 11.88 to 35.63 mg/L $MgSO_4 \cdot 7H_2O$, 0.88 to 2.63 mg/L urea, 32.5 to 97.50 μl/L $HNO_3$, 7.50 to 22.50 μl/L $H_3PO_4$ as major nutrients group (A solution), and water, preferably distilled water. Preferably, any or each major nutrient ingredient in the culture medium is present in an amount within 0.50, 0.75, 1.00, 1.25, 1.5, 1.75 to 2.00 times the amount indicated in Table 1.

The culture medium may in addition to the major nutrients described above, further comprise, consist essentially of, or consist of at least one of, preferably all of, micronutrients: $FeCl_3 \cdot 6H_2O$, $H_3BO_3$, $Co(NO_3)_2 \cdot 6H_2O$, $K_2Cr_2O_7$, $CuSO_4 \cdot 5H_2O$, $MnSO_4 \cdot H_2O$, $ZnCl_2$, $(NH_4)_6Mo_7O_{24} \cdot 4H_2O$, $Na_2$-EDTA or HCl, preferably in the following concentration ranges: 1.75 to 5.25 mg/L $FeCl_3 \cdot 6H_2O$, 0.50 to 1.50 mg/L $H_3B_3$, 0.13 to 0.38 mg/L $Co(NO_3)_2 \cdot 6H_2O$, 0.05 to 0.15 mg/L $K_2Cr_2O_7$, 0.05 to 0.15 mg/L $CuSO_4 \cdot 5H_2O$, 0.13 to 0.38 mg/L $MnSO_4 \cdot H_2O$, 0.38 to 1.13 mg/L $ZnSO_4 \cdot 6H_2O$, 0.13 to 0.38 mg/L $(NH_4)_6Mo_7O_{24} \cdot 4H_2O$, 0.50 to 1.50 mg/L $Na_2$-EDTA, and 0.50 to 1.50 μl/L HCl (from B solution, micronutrient group).

The culture medium in addition to the major and micro nutrients above may further comprise 0.88 to 1.2 mg/L thiamine, 0.0024 to 0.0036 mg/L+D-biotin, and 0.00008 to 0.00012 mg/L cyanocobalamin.

Culture medium (1× or other strengths) may be produced by dilution of stock solutions "A" (major nutrients), "B" (micronutrients) and "C" (vitamins) in water or sea water, for example, in natural seawater having salinity of 30 ppt. In some embodiments, described herein, stock solution A is 1,000×, stock solution B is 10,000× and stock solution C is 10,000× based on the concentrations of the major nutrients, micronutrients, and vitamins disclosed above. Typically, the solid components such as salts are described in concentrations of g/L or mg/L and the liquid components such as acids in ml/L or μl/L.

In some embodiments, the culture medium may be formulated with sterile, filtered or autoclaved water. In other embodiments it may be formulated with non-sterile water such as sea water, riparian water, well water, tap water or distilled water that has not been filtered or autoclaved. Water used in the medium describes herein may have a salinity from 0, 10, 20, 30, 40, 50 to >50 ppt. In some embodiments, seawater having a salinity ranging from 25, 30 or 35 ppt may be used. In a preferred embodiment, the culture medium is prepared using water that has had its pH lowered to pH 2.5, 2.75, 3.0, 3.25, 3.5, 3.75, 4.0, 4.5 or 5.0 or below and then raised to at least pH 6.0, 6.5, 7.0, 7.5 or 8.0 prior to inoculation of the culture medium with *Haematococcus* or other microalgae. Such waters may be kept at a low pH until suitable reductions in contaminants are attained, for example, 5, 10, 15, 30, or 60 mins, or 2, 4, 6, 8, 10, 12, 18, 24 or >24 hours.

This method may further comprise a culture medium that has been supplemented or pH adjusted using one or more exogenous (to the medium as prepared in ambient air) combustion gases, such as those obtained from a coal-fired power plant. In some embodiments, at least 1, 2, 5, 10, 15, 20, to 25 vol % $CO_2$ as a combustion gas is incorporated into, contacted with, or used to adjust the pH of the culture medium. In other embodiments, the combustion gas comprises carbon dioxide, carbon monoxide, and one or more nitrogen oxides ("$NO_x$") or sulfur oxides ("$SO_x$") which are incorporated into the medium or used to adjust its pH. The combustion gases may be obtained from the combustion of coal, for example, from burning coal in a power plant. Thus, in some preferred embodiments, the culture medium described herein will further contain or be pH adjusted with one or more combustion gases or dissolved or infused combustion gases such as carbon dioxide, carbon monoxide, a nitrogen oxide, and/or a sulfur oxide. The pH may be adjusted using combustion gases like $CO_2$ for example to or towards pH 5, 5.5, 6, 6.5, 7, 7.5 or 8.

This method typically involves the culturing of the *Haematococcus*, such as a strain which has 18s or ITS2 rDNA that is at least 98, 99, 99.5, 99.9, or <100% identical to the 18s or ITS2 rDNA of *Haematococcus* sp. KAU-01. Preferably it involves culturing *Haematococcus* sp. KAU-01, a subculture thereof, or a genetically or epigenetically modified form thereof. In one embodiment, a high passage number strain *Haematococcus* sp. KAU-01 that has been passaged in AAHKAU medium 5, 10, 15, 20, 30 or more times may be used. Similarly such a high passage number strain of *Haematococcus* sp. KAU-01 may be one that has been passaged 5, 10, 15, 20, 30 or more times in AAHKAU medium that has been contacted with, infused or incorporated with, carbon dioxide or other combustion gases.

In some embodiments, the culture medium during or after growth of *Haematococcus* will be filtered or otherwise treated to decrease or remove eicosapentaenoic acid (EPA) and cell debris and other growth inhibitors from the culture medium. This may be accomplished by sedimenting or filtering the culture to retain viable *Haematococcus* while removing soluble components that pass through the filter.

In some embodiments, this method comprises replacing at least 5, 10, 15, 20, 25 or 30 or >30% of spent culture medium with fresh culture medium and adjusting the pH of the culture medium to range from pH 6, 6.5, 7, 7.5, to 8.5, preferably to about pH 7.5.

In some embodiments, a *Haematococcus* sp., such as *Haematococcus* sp. KAU-01 will be inoculated at or grown to a cell abundance (cells/L) of >0, 0.1, 0.2, 0.5, 1, 2, 3, 4, 5, 6, 7, 8, 9, 10, 11, 12, 13, 14, 15 or >15 prior to harvest of cells by sedimentation, centrifugation, or filtration. Harvested cells may subsequently be washed in culture medium or water or other suitable buffer, and/or dried. Such a culture may produce an amount of dry biomass (g/L) ranging from >0, 0.5, 1, 1.5, 2, 2.5 or >2.5 g/L.

Another embodiment of the invention is directed to a culture medium comprising, consisting essentially of, or consisting of the media described above. In some embodiments, it will comprise, consist essentially of or consist of the macronutrients, micronutrients and vitamins described in Table 1 or a medium containing these nutrients at concentrations of 0.8, 0.9, 0.95, 1, 1.05, 1.10 or 1.20 times the values of one or more or all medium components described in Table 1. It may also be formulated according to Tables 4A and 4B or by any of the formulations in Table 4C. The medium may be made with sea water or other sources of water, such as those described above. The water component of the medium may be treated at low pH as described above to remove contaminating or competing microorganisms prior to inoculation with *Haematococcus*. For example, water pH may be lowered to pH 3.5 or below and then raised to or towards a pH of 6.5, 7.0 or 7.5 or more prior to inoculation with *Haematococcus*.

The method disclosed herein may be practiced in a bioreactor system or photobioreactor system comprising a bioreactor, the culture medium disclosed herein, and viable *Haematococcus*. Such a bioreactor system may further contain filter suitable for removing eicosapentaenoic acid (EPA) and cell debris from the culture medium or for separating viable *Haematococcus* from spent medium, and retaining viable *Haematococcus*.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

FIGS. 8A-8B. Maps of sample collection area for *Haematococcus* sp. KAU-01.

FIGS. 8C-8D. Terrain of sample collection area at Green Valley, Jeddah, the Kingdom of Saudi Arabia.

FIG. 9. Green vegetative cell with (a) two flagella, (b) trilaminar sheath, (c) cytoplasmic strands and (e) pyrenoids as observed under inverted light microscope.

FIGS. 10A-10F. Life cycle from green, vegetative motile form to non-motile aplanospore.

FIG. 10A: shows green, motile vegetative flagellated cells.

FIG. 10B shows large aplanospores with red astaxanthin at the center and spreading towards circle and green chlorophyll a around peripheries.

FIG. 10C shows fully red color aplanospore.

FIGS. 10D and 10E depict asexual reproduction of aplanospore.

FIG. 10F shows daughter cell are coming out by breaking aplanospore cell wall with little astaxanthin.

FIGS. 13A-13F. Growth and dry biomass production of *Haematococcus* sp. KAU, culture in square design combinations of A and B stock solutions. See Table 4A-4C below for media formulations for A1-A5 and B1-B5.

FIG. 13A. Dry biomass produced by culture in major nutrient concentrations A1 in combination with minor nutrient concentrations B1-B5.

FIG. 13B. Dry biomass produced by culture in major nutrient concentrations A2 in combination with minor nutrient concentrations B1-B5.

FIG. 13C. Dry biomass produced by culture in major nutrient concentrations A3 in combination with minor nutrient concentrations B1-B5. Combination A3B3 provided superior results compared to other A3 combinations.

FIG. 13D. Dry biomass produced by culture in major nutrient concentrations A4 in combination with minor nutrient concentrations B1-B5.

FIG. 13E. Dry biomass produced by culture in major nutrient concentrations A5 in combination with minor nutrient concentrations B1-B5.

FIG. 13F. Dry biomass produced by culture in major nutrient concentrations A3 in combination with minor nutrient concentration B3 ("A3B3") compared to conventional media OHM, RM, Basal and HK. Combination A3B3 provides superior results compared to all comparative media.

DETAILED DESCRIPTION OF THE INVENTION

Figure 1:
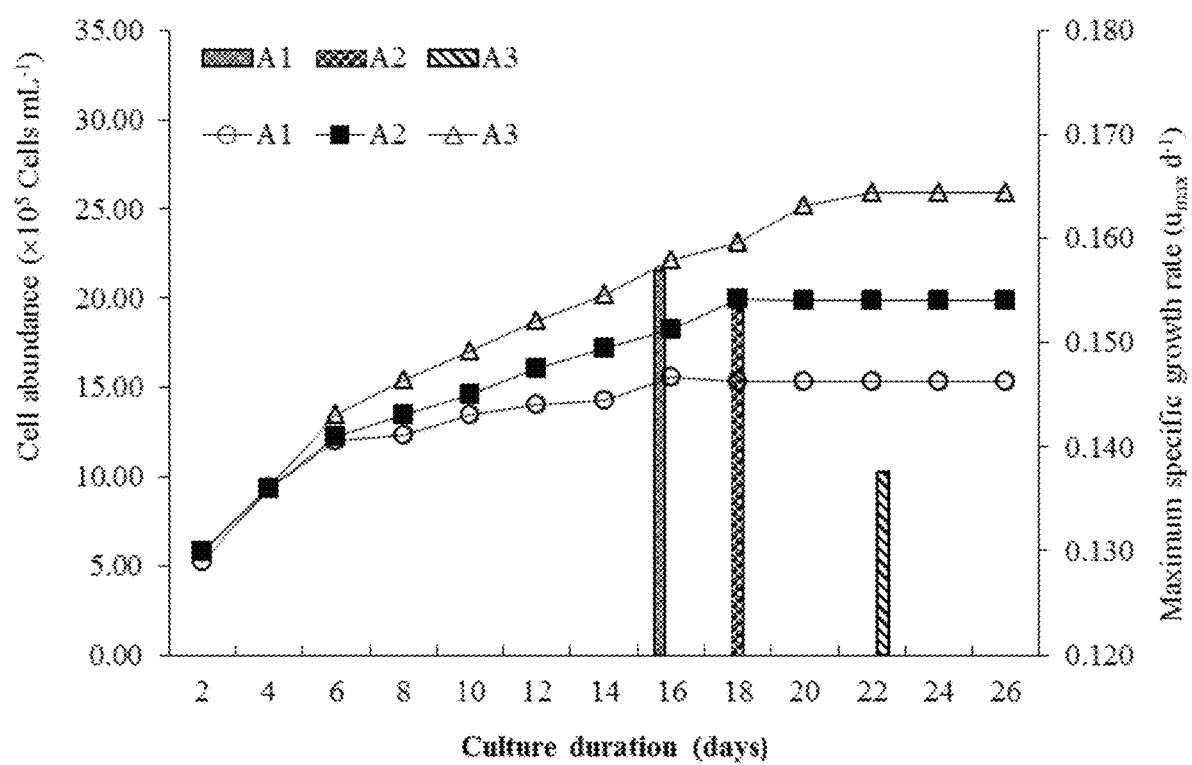
FIG. 1. Variation in maximum specific growth rate ($u_{max}$ $d^{-1}$) and growth curves with cell abundance ($\times 10^5$ cells $mL^{-1}$) of *Haematococcus* sp. KAU cultured in AAHKAU medium within 'A' culture group. A1: continuous aeration with normal air; A2: continuous aeration with normal air, pH was maintained at pH 7.5 by injecting amounts of stock solutions A and B; A3: continuous aeration with normal air, 20% media replacement on alternate days.

The inventors compared several different formulations of culture medium for growing *Haematococcus*. They found that one culture medium designated Affan-Adnan *Haematococcus* sp. King Abdulaziz University ("AAHKAU" medium) significantly reduced cell wall breakage during cultivation of *Haematococcus* microalgae and that the growth and biomass of particular strains or isolates of *Haematococcus*, such as *Haematococcus* sp. KAU-01, were significantly increased.

One embodiment of the invention is directed to a culture medium contains the major nutrients group $NaNO_3$, $KNO_3$, $Ca(NO_3)_2$, $Mg(NO_3)_2 \cdot 6H_2O$, $K_2HPO_4$, $KH_2PO_4$, $K_2SO_4$, $MgSO_4 \cdot 7H_2O$, urea, $HNO_3$ and $H_3PO_4$. The same molar amounts of salts equivalent to those in the above hydrated compounds may be used, for example, from an anhydrous salt or from a salt having a different degree of hydration.

Major nutrient concentrations preferably range as follows:
187.50 to 562.50 mg/L $NaNO_3$,
37.50 to 112.50 mg/L $KNO_3$,
12.50 to 37.50 mg/L $Ca(NO_3)_2$,
27.50 to 82.50 mg/L $Mg(NO_3)_2 \cdot 6H_2O$,
22.50 to 67.50 mg/L $K_2HPO_4$,
20.00 to 60.00 mg/L $KH_2PO_4$,
5.00 to 15.00 mg/L $K_2SO_4$,
11.88 to 35.63 mg/L $MgSO_4 \cdot 7H_2O$,
0.88 to 2.63 mg/L urea,
32.50 to 97.50 µl/L $HNO_3$, and
7.50 to 22.50 µl/L $H_3PO_4$.

Preferably a concentration is selected that is midrange or approximately midrange of the above ranges. One example of such major nutrient concentrations is shown by Table 1, A-solution in culture medium.

Three stock solutions for preparation of AAHKAU medium were made: "A" for major nutrients, "B" for micronutrients and "C" for vitamins.

For preparation of concentrated stock solution "A" (1,000×) the following amounts of ingredients were used:
$NaNO_3$ (375.00 g),
$KNO_3$ (75.00 g),
$Ca(NO_3)_2$ (25.00 g),
$Mg(NO_3)_2 \cdot 6H_2O$ (55.00 g),
$K_2HPO_4$ (45.00 g),
$KH_2PO_4$ (40.00 g),
$K_2SO_4$ (10.00 g),
$MgSO_4 \cdot 7H_2O$ (23.75 g),
Urea (1.75 g),
$HNO_3$ (65.00 ml/L) and
$H_3PO_4$ (15 ml/L).

These ingredients were diluted in autoclaved distilled water and the final volume was made 1 L. Thereafter, five different concentrations of major nutrients solutions were tested for growth of *Haematococcus* KAU sp. For five concentrations, the amount stock solution added to freshwater were 0.5, 0.75, 1.00, 1.25 and 1.50 ml/L to prepare 'A1', 'A2', 'A3', 'A4' and 'A5' culture medium, respectively.

For concentrated stock solution "B" (10,000×) the specified amounts of the following ingredients were mixed:
$FeCl_3 \cdot 6H_2O$ (35.00 g),
$H_3BO_3$ (10.00 g),
$Co(NO_3)_2 \cdot 6H_2O$ (2.50 g),
$K_2Cr_2O_7$ (1.00 g),
$CuSO_4 \cdot 5H_2O$ (1.00 g),
$MnSO_4 \cdot H_2O$ (2.50 g)
$ZnSO_4 \cdot 6H_2O$ (7.50 g),
$(NH_4)_6Mo_7O_{24} \cdot 4H_2O$ (2.50 g),
$Na_2$-ETDA (10.00 g) and
HCl (10.00 ml).

These ingredients were diluted into filtered natural seawater having salinity of 30.00 ppt and final volume was made 1 L. Then, 50, 75, 100, 125, or 150 µl/L of "B" solution was respectively added to A1', 'A2', 'A3', 'A4' and 'A5' culture medium.

Similarly, stock solution of "C" (10,000×) was prepared by diluting of thiamine (10.00 g/L), +D-biotin (0.03 g/L) and cyanocobalamin (0.001 g/L) into boiled autoclaved distilled water and finally the volume was made 1 L. Then 100 µl/L of "C" solution was added to the culture of A1', 'A2', 'A3', 'A4' and 'A5' culture medium, respectively.

Typically, 1 ml of the 1,000× stock solution 1, 0.1 ml of the 10,000× stock solution B, and 0.1 ml of the 10,000× stock solution B are diluted in water up to 1 L to form 1×AAHKAU medium. However, other amounts of these stock solutions may be used to produce mediums with a lower or higher concentration of particular components. The exact amounts of each ingredient in the stock solutions A, B and/or C or in the 1×AAHKAU preparation from stock solutions may vary by ±1, 2, 3, 4, 5, 6, 7, 8, 9 or 10%.

In further embodiments, this culture medium includes one or more of the following micronutrients $FeCl_3 \cdot 6H_2O$, $H_3BO_3$, $Co(NO_3)_2 \cdot 6H_2O$, $K_2Cr_2O_7$, $CuSO_4 \cdot 5H_2O$, $MnSO_4 \cdot H_2O$, $ZnSO_4 \cdot 6H_2O$, $(NH_4)_6Mo_7O_{24} \cdot 4H_2O$, $Na_2$-EDTA and HCl.

Micronutrient concentrations preferably range as follows:
1.75 to 5.25 mg/L $FeCl_3 \cdot 6H_2O$,
0.50 to 1.50 mg/L $H_3BO_3$,
0.13 to 0.38 mg/L $Co(NO_3)_2 \cdot 6H_2O$,
0.05 to 0.15 mg/L $K_2Cr_2O_7$,
0.05 to 0.15 mg/L $CuSO_4 \cdot 5H_2O$,
0.13 to 0.38 mg/L $MnSO_4 \cdot H_2O$,
0.38 to 1.13 mg/L $ZnSO_4 \cdot 6H_2O$,
0.13 to 0.38 mg/L $(NH_4)_6Mo7O_{24} \cdot 4H_2O$,
0.50 to 1.50 mg/L $Na_2$-EDTA, and
0.50 to 1.50 µl/L HCl.

Preferably a concentration is selected that is midrange or approximately midrange of an above range. One example of such a concentration appears in Table 1, B-solution in culture medium.

In still other further embodiments, the culture medium further includes one or more vitamins such a thiamine, D-biotin and/or cyanocobalamin preferably within the ranges of 0.8 to 1.2 mg/L thiamine, 0.0024 to 0.0036 mg/L+D-biotin, and 0.00008 to 0.00012 mg/L cyanocobalamin.

Preferably a concentration is selected that is midrange or approximately midrange of the above ranges such as those concentrations shown by Table 1, Solution C.

TABLE 1

Chemical concentrations of AAHKAU medium (1X) for culture of *Haematococcus* sp KAU.
1X AAHKAU Medium

| A-solution Chemicals | Conc. mg/L | B-Solution Chemicals | Conc. mg/L | C-Solution Chemicals | Vitamins mg/L |
|---|---|---|---|---|---|
| $NaNO_3$ | 375.00 | $FeCl_3 \cdot 6H_2O$ | 3.50 | Thiamine | 1.00 |
| $Ca(NO_3)_2$ | 25.00 | $H_3BO_3$ | 1.00 | +D-biotin | 0.003 |
| $Mg(NO_3)_2 \cdot 6H_2O$ | 55.00 | $Co(NO_3)_2 \cdot 6H_2O$ | 0.25 | Cyanocobalamin | 0.0001 |
| $K_2HPO_4$ | 45.00 | $K_2Cr_2O_7$ | 0.10 | | |
| $KH_2PO_4$ | 40.00 | $CuSO_4 \cdot 5H_2O$ | 0.10 | | |
| $KNO_3$ | 75.00 | $MnSO_4 \cdot H_2O$ | 0.25 | | |
| $K_2SO_4$ | 10.00 | $ZnSO_4 \cdot 6H_2O$, | 0.75 | | |
| $MgSO_4 \cdot 7H_2O$ | 23.75 | $(NH_4)_6Mo_7O_{24} \cdot 4H_2O$ | 0.25 | | |
| Urea | 1.75 | $Na_2$-ETDA | 1.00 | | |
| $HNO_3$ | 65.00 μl/L | HCl | 1.00 μl/L | | |
| $H_3PO_4$ | 15.00 μl/L | | | | |

In some embodiments, a culture medium, especially AAHKAU medium, may be prepared using acidified water, such as water or seawater at a pH of 2, 3, 4, 5, 6 or <7, preferably about pH 2.5 to 3.5 or at about pH 3.0. The pH of the water prior to use in a medium or the pH of the medium prepared with the acidified water may then be brought up to its final value, such as between 6 and 8, preferably about pH 7 to 7.5. Surprisingly, the inventors found that use of acidified water in place of sterile water to produce AAHKAU medium produced significant yields of biomass compared to other sterile media. It is believed that the enhanced biomass is due to suppression or eradication by acid hydrolysis of microorganisms that compete with *Haematococcus* and thus reduce biomass produced by *Haematococcus*.

In some embodiments, the culture medium, such as AAHKAU medium may be formulated, diluted, or concentrated to contain 10, 20, 30, 40, 50, 60, 70, 80, 90, 100, 110, 120, 130, 140 150 or >150% of its 1× concentrations of one or more, or all, of its ingredients. Dilution or concentration of the medium and/or adjustment of temperature, pH or other culture conditions may be used to modulate the rate of growth or production of biomass by *Haematococcus* when grown in the diluted medium or culture medium supplemented with more or less concentrated AAHKAU medium. In one example, AAHKAU medium is used at a concentration, such as in a more or less concentrated form to properly adjust the pH of an ongoing culture, for example, an amount sufficient to adjust the pH to about 7.5. Preferably, the concentration of AAHKAU medium concentrations of ingredients in AAHKAU medium or similar media are not increased or reduced by more than 1, 2, 3, 4, 5, 6, 7, 8, 9, 10, 15 or 20%. Preferably, AAHKAU medium is used at about a 1× concentration to culture *Haematococcus*.

A culture media, such as AAKAU medium, when used to culture *Haematococcus* in the presence of combustion gases, may be formulated with or further contain infused or dissolved combustion gases including, but not limited to, carbon dioxide, carbon monoxide, nitrogen oxides, and/or sulfur oxides as well as volatile organic compounds. As used herein the term "combustion gas" describes the kinds of gases produced by combustion which may be produced by combustion or obtained from some other source. The culture medium disclosed herein may incorporate the same kinds of gases produced by combustion of fossil fuels, but which are obtained from other sources.

The term "flue gas" refers to the kinds of gases commonly found in flue gases from combustion chambers whatever their source. Flue gases are one type of combustion gases resulting from combustion fossil fuels which usually contain carbon dioxide, carbon monoxide, $NO_x$ and sulfur dioxides ($SO_x$). These gases result from the burning of coal, petroleum, natural gas, gasoline, diesel, fuel oil, or other petrochemicals. Coals include peat, lignite, bituminous, and anthracite coals. Low (<3% by weight sulfur) and high sulfur (≥3, 4, 5, 6, 7, 8, 9, 10% by weight sulfur) coals may also provide the gases for incorporation into a medium of the invention. Flue gases are gases which can be produced when natural gas, fuel oil, coal, wood, cellulose wastes (e.g., grass, palm fronds, paper, and cardboard) or any other fuel is combusted in an industrial furnace, a steam generator in a fossil fuel power plant, or other combustion zone or chamber. Typically, flue gases consist of mostly nitrogen, carbon dioxide ($CO_2$), carbon monoxide, nitrogen oxides, sulfur oxides, oxygen, and water vapor as well as small percentages of various of pollutants, such as particulate matter like soot, carbon monoxide, nitrogen oxides, and sulfur oxides; see Milton R. Beychok, *Fossil fuel combustion flue gases*, ENCYCLOPEDIA OF EARTH, 2012 (incorporated by reference). Flue gases include so-called greenhouse gases such as carbon dioxide, methane and water vapor which can retain heat in the environment.

Combustion gases may be mixed with other gases or trapped in liquid or solids prior to incorporation into a culture medium as disclosed herein. For example, carbon, nitrogen and/or sulfur oxides may be trapped in a liquid or solid byproduct obtained from a wet or dry scrubber prior to incorporation into a medium. Alternatively, prior to incorporation into a medium combustion gases may be purified by removal of certain components, such as carbon, sulfur or nitrogen oxides, volatiles or particles.

In some embodiments, combustion gases may be admixed with air or other gases, partitioned so as to increase a concentration of one or more gases or decrease the concentration of one or more gases. They may be filtered, scrubbed, or modified prior to their incorporation or dissolution into a culture medium, for example, water vapor or heavy metals or solid particles may be removed or their temperature adjusted to facilitate incorporation into a medium or to maintain the temperature of a culture medium within a range suitable for growth of *Haematococcus*. One or more contaminants, such as heavy metals, carbon, ash, or other products of combustion may be removed from or separated from combustion gases or their mixtures or derivatives prior to incorporation into a culture medium. Heavy metals include arsenic, antimony, lead, zinc, manganese, nickel, copper, and chromium. Reductions ranging from <5%, 10, 20, 30, 40, 50, 60, 70, 80, 90, 95, <100, or 100% of these metals may be made to lessen the impact of these metals on the growth of microalgae or the contamination of biomass produced by microalgae. Heavy metals may be captured and removed from combustion gases by methods known in the art include those described by Chen, et al., SCIENCE OF THE TOTAL ENVIRONMENT, 1999, 228 (1): 67-77 (incorporated by reference) or Li, et al., *Research on characteristics of heavy metals (As, Cd, Zn) in coal from southwest China and prevention method by using modified calcium-based materials*, FUEL, 2016, 186:714-725 (incorporated by reference).

Typically, combustion gases are incorporated into a culture medium in amounts that would exceed their concentrations when absorbed under similar conditions from normal air which contains trace amounts of carbon dioxide, carbon monoxide, and other gases. For example, a medium containing gases from combustion of coal may contain at least 25, 50, 100, 200, 300, 400, 500 or >500% more carbon dioxide, carbon monoxide, oxides of nitrogen or oxides of sulfur than the same medium exposed only to normal, dry air which contains around 0.04% carbon dioxide or about 0.2 ppm of carbon monoxide. In other embodiments, the culture medium may absorb combustion gases from polluted air, for example, from smoggy air containing $NO_x$ or $SO_x$.

In one embodiment, combustion gases for a coal-fired power plant are taken from the flue or chimney into a reserve tank with pressure and brought to approximately ambient or room temperatures and then supplied to AAHKAU culture medium to adjust its pH to about 7 to 8, preferably about pH 7.5.

Culture medium pH, salt content, osmolality, or temperature may be adjusted after addition of carbon dioxide or other combustion gases or their byproducts (e.g., processed or scrubbed gases, etc.). Preferably, these parameters match those of AAHKAU medium as disclosed herein or match within about ±5, 10 or 20% thereof.

*Haematococcus* may be cultured in AAHKAU medium in a variety of different ways including with or without the presence of combustion gases, in outside pools or facilities, inside of controlled bioreactors, or absence of other microorganism or microalgae. Other microalgae, predatory protozoans, molds, and most bacteria may be removed as disclosed herein by acidifying culture water or fluids, or by filtration, pasteurization, and/or bleaching (chlorination-dechlorination). Suitable bioreactors for cultivation of *Haematoccus* sp. KAU-01 may be selected by those skilled in the art. Examples of such bioreactors and methods of use are commercially available, for example, from Industrial Plankton, Canada, and are incorporated by reference to Duan, et al., *Chapter 2—Bioreactor design for algal growth as a sustainable energy source*, REACTOR AND PROCESS DESIGN IN SUSTAINABLE ENERGY TECHNOLOGY, 2014, Pages 27-60; or to Kaewpintong, et al., *Photoautotrophic high-density cultivation of vegetative cells of Haematococcus pluvialis in airlift bioreactor*, BIORESOURCE TECHNOLOGY, January 2007, 98(2)2, 288-295.

*Haematococcus* is typically cultured in the presence of light which may be natural, reflected, focused or concentrated sunlight or, alternatively, artificial light or a mixture of natural and artificial light having a wavelength suitable for culture of *Haematococcus* sp. The wavelength of the used to cultivate microalgae is not limited as long as it can be adsorbed and used by the microalgae to grow or produce biomass. Visible light having a wavelength ranging from 380, 400, 450, 500, 550, 600, 650, 700, 750 to 780 nm may be used. The amount or intensity of the light used to cultivate the microalgae is not limited as long as it is sufficient for the microalgae to grow or produce biomass. For example, respective photosynthetic photon flux densities (PPFD) in the vicinity of a light irradiation surface of the culture solution may range from 5 $\mu mol/m^2/s$ to 200 $\mu mol/m^2/s$, preferably 10 $\mu mol/m^2/s$ to 100 $\mu mol/m^2/s$, and more preferably 20 $\mu mol/m^2/s$ to 70 $\mu mol/m^2/s$. Illumination of the microalgae may be continuous, periodic or intermittent. Preferred illumination periods range from 1, 2, 4, 6, 8, 10, 12, 14, 16, 18, 20, 22 or 24 hours and may be cyclic or non-cyclic. Advantageously, the microalgae may be illuminated on a 12 hour light and 12 hour dark cycle or illumination may be tuned to natural seasonal light and dark cycles.

*Haematococcus* sp. is typically grown in the presence of light and at a temperature suitable for its growth and/or production of biomass, for example, at a temperature ranging from 15, 16, 17, 18, 19, 20, 21, 22, 23, 24, 25, 26, 27, 28, 29, 30, 31, 32, 33, 34 or 35° C.

In some embodiments, astaxanthin production is triggered by stressing the *Haematococcus* culture, for example, by nitrogen deprivation, change in pH or a change in salinity. Stress will start within culture medium when pH rises and the motile swimming cells turn to cysts which finally become red cysts. Stress can trigger the production of cysts containing astaxanthin.

Culture methods include batch, fed batch and continuous culture modes. Microalgae may also be cultured outdoors in pools or ponds which may be periodically or continuously fed with medium components or adjusted for pH, salt concentration, temperature or other growth related parameters.

Fed-batch culture is an operational technique where one or more nutrients or substrates, such as culture medium components or stock, are fed or supplied to a bioreactor during cultivation and in which the viable microalgae and cultured products often remain in the bioreactor until the end of a run. This permits addition of nutrients for growth of the microalgae as well as for removal of spent medium containing growth inhibitors, metabolites, or cellular debris that inhibit growth, production of, or accumulation of biomass. As disclosed herein advantageously *Haematococcus* sp. KAU-01 is cultivated in a fed-batch mode.

Additional medium or stock may be intermittently, periodically or continuously added to the culture in a bioreactor or other container, for example, 10, 15, 20, 25, 30 or >30% of the spent culture medium may be replaced every 1, 2 or 3 days or the pH may be adjusted by addition of acidic stock. In some embodiments, additional medium or nutrients may be added exponentially increasing amounts based on the density of viable *Haematococcus* in the culture.

In some embodiments, a fed-batch culture of *Haematococcus* sp. will replace or add 1, 2, 5, 10, 15, 20, 25, 30, 35, 40, 45, 50, 55, 60, 65, 70, 75, 80, 85, 90, 95 or 100% by volume of the spent culture medium with fresh culture medium. Culture medium may be replaced every 1, 2, 4, 6, 12, 24, 36, 48, 60, 72, or >72 hours or within any intermediate period within this range. Advantageously, about 10, 15, 20, 25 or 30% of the spent culture medium is replaced every other day after an initial culture period of 1, 2, 3, 4, 5 or 6 days. The temperature of the culture medium may be adjusted to fall within the range of 15, 20, 25, to 30° C. The pH of the culture medium may be adjusted before, during, or after feeding with fresh medium, for example, by adding acid, base, buffer, culture medium or stock or combustion gases to bring the culture pH to 5, 5.5, 6, 6.5, 6.6, 6.7, 6.8, 6.9, 7, 7.1, 7.2, 7.3, 7.4, 7.5, 8, >8 or any intermediate value within this range.

Advantageously, methods of fed-batch or continuous culture can involve removal of spent medium containing eicosapentaenoic acid (EPA) and cell debris without removing viable *Haematococcus*/ This may be accomplished by filtration of the culture medium to retain viable *Haematococcus* but to remove EPA or cell debris or by sedimentation to separate spent medium from microalgae. Spent medium which may contain other growth inhibitory substances is typically removed by filtration through one or more filters that retain viable *Haematococcus* sp. KAU-01 cells, but which permit passage of growth inhibitory substances such as eicosapentaenoic acid (EPA) and cellular debris. Cells may range in size from about 5, 10, 15, 20 to 25 microns and some representative filter mesh sizes range from about 1, 2, 3, 4, 5, 6, 7, 8, 9, 10, 11, 12, 13, 14, 15, 16, 17, 18, 19, 20, 21, 22, 23, 24 or 25 microns. As shown herein a filter bag or phytoplankton net mesh size of about 5 or 10 microns is suitable for retaining viable *Haematococcus* sp. KAU-01 cells. Other conventional or commercially available algae filters or scrubbers may be used. In some embodiments, other separation modes may be used including centrifugation or sedimentation to separate or partially separate viable cells from other culture components.

Following culture or fed-batch culture, microalgae are harvested, for example, by filtration, sedimentation, or centrifugation. Products may be recovered from the microalgae or from the spent medium.

Harvested microalgae may be used to make biofuel, nutraceuticals such as omega three fatty acids supplements, glycoproteins, pigments or dyes, or as animal or aquaculture feeds. Biological products made by microalga such as *Haematococcus* include beta-carotene, astaxanthin, canthaxanthin, lutein, other polyisoprenoids, EPA and other fatty acids. These may be harvested or recovered at a point in the alga lifecycle where they are maximally expressed or at a point where their purity is high at a time when little degradation or chemical transformation of the desired product has occurred, or when it is easy to isolate them from other algae components, for example, beta-carotene and lutein and other materials produced during the vegetative state may be harvested when an algae is in a green vegetative state and astaxanthin and other materials typically produced or accumulated in cysts from the cysts.

In some embodiments, *Haematococcus* or more specifically *Haematococcus* sp. KAU-01, may be cultured outside, for example, in an outdoor circulating pool exposed to sunlight or reflected sunlight which containing a suitable medium, such as AAHKAU medium or diluted or modified AAHKAU medium. Preferably, such culturing is performed at a pH ranging from 7.0-8.0, advantageously at an adjusted pH of 7.5 and may be accompanied by intermittent, continuous or periodic feeding as disclosed herein.

Another embodiment of the invention is directed to a bioreactor that includes a culture medium disclosed herein, at least one, two or three ports to input for one or more gases or derivatives of gases produced by combustion in an amount greater than present in air, at least one, two or three ports to add fresh culture medium, at least on, two or three ports equipped with a filter, centrifuge or other sedimentation device to remove spent culture medium and/or cellular debris without removing viable *Haematococcus*. In one embodiment of the bioreactor, spent culture medium and/or cellular debris are removed by passing them through a bag net filter having about a 1, 2, 3, 4, 5, 6, 7, 8, 9, or 10 μm mesh size, preferably about 5 μm.

Typically a bioreactor will include a container, such as a tank and a light source, where the tank contains a culture medium and dispersed algal cells such as *Haematococcus* sp. KAU-01 cells. The algal cell culture may have a concentration of greater than 0.05, 0.1, 0.2, 0.3, 0.4, 0.5, 0.6, 0.7, 0.8, 0.9, 1.0, 2.0 or >2.0 g/l in the culture medium. A bioreactor may have a paddle or other kind of agitator, mixer, pump, or circulator to keep the cells in suspension.

A photobioreactor ("PBR") is a bioreactor which incorporates a light source and may be used to cultivate *Haematococcus* sp. KAU-01 cells. Virtually any translucent container may be called a PBR and in some embodiments the PBR is a tank, a polyethylene or other clear or translucent plastic sleeve or gag or clear or translucent tubes, such as glass or plastic tubes. This term typically describes a closed system as opposed to an open tank or pond. During culture *Haematococcus* sp. may be exposed to light or dark conditions, for example, to 1, 2, 3, 4, 5, 6, 7, 8, 9, 10, 11, 12, 13, 14, 15, 16, 17, 18, 19, 20, 21, 22, 23 or 24 hours of light or dark, preferably to a cycle of about 12 hours light and 12 hours dark.

A closed PBR system generally provides all the nutrients and micronutrients necessary for algae growth and may operate using AAHKAU medium or its variants disclosed herein. A PBR can operate in "batch mode", which involves restocking the reactor after each harvest, but it is also possible to grow and harvest microalgae periodically or continuously. Continuous operation requires precise control of all elements to prevent culture collapse. The grower typically provides sterilized water, nutrients, air, and carbon dioxide or other greenhouse or flue gases at a predetermined rate. Algae grown in the log phase is generally of higher nutrient content or better at removing or remediating flue or greenhouse gases than old senescent algae.

In some embodiments, *Haematococcus* sp. KAU-01 cells are grown in a photobioreactor using procedures and/or equipment that permit removal of growth inhibitory substances. In other embodiments, *Haematococcus* sp. KAU-01 may be grown under condition where EPA and cellular debris are continuously removed, for example, by growing it in flat transparent porous bags that retain viable *Haematococcus* sp. KAU-01, but permit outward diffusion of EPA and cellular debris or that permit sedimentation of cellular debris. These porous bags may be continuously, periodically or intermittently supplied with fresh culture medium such as AAHKAU medium, a modified, concentrated or diluted AAHKAU medium.

The bioreactor may further comprise, when in use, one or more *Haematococcus* sp. such as *Haematococcus* sp. KAU-01 or a subculture, genetically or epigenetically modified version, mutant or variant thereof as disclosed herein.

Biomass from the cultured microalgae may be recovered by filtration, centrifugation, and/or sedimentation of the culture medium or other liquid containing the biomass. Biomass recovered from culture medium may be further washed, rinsed, dried, concentrated or otherwise processed, for example, to isolate a chemical component it contains such as a fatty acid, pigment, astaxanthin, or other nutraceutical product, to place it in a form for processing into biodiesel or other fuel, to place it in a usable form transport, or to put in into a form suitable for use as an animal or aquaculture feed. Biological products made by microalga such as *Haematococcus* include beta-carotene, astaxanthin, canthaxanthin, lutein, other polyisoprenoids, EPA and other fatty acids. Other biomass which incorporates carbon, nitrogen, sulfur or other elemental components of combustion gases is also produced.

*Haematococcus* is a genus of algae in the family Haematococcaceae. The strain *Haematococcus* sp. KAU-01 is a previously unknown unicellular red microalga isolated by the inventors from the arid tropical environment of Jeddah, the Kingdom of Saudi Arabia (KSA). Morphological analysis of this isolate revealed that it was a motile unicellular biflagellated green microalga with semi-transparent trilaminar sheath between its cell wall and cytoplasm. After blooming in a harsh environment, *Haematococcus* sp. KAU-01 forms a non-motile, thick-walled palmelloid or red aplanospore. In some conventional culture media, cell wall lysis occurred above pH 9. However, the inventors found that cell abundance and biomass production by this strain was almost double in the AAHKAU medium described herein compared to other conventional culture media for *Haematococcus*.

The term *Haematococcus* sp. KAU-01 describes the particular unspecified species isolated from a hot, tropical climate and characterized by the inventors. It may exhibit genetic changes that adapt it to a hotter more tropical environment than other *Haematococcus* sp. *Haematococcus* sp. KAU-01 has been deposited at ATCC Patent Depository, 10801 University Boulevard, Manassas, Va. 20110 under Patent Deposit Number PTA-127272. The inventors have isolated the original isolate from other microalgae as well as produced a highly passaged strain derived from *Haematococcus* sp. KAU-01 (hp) which may exhibit genetic and epigenetic changes compared to the original isolate. This high passage number strain has become stable after several passages where more than 80% of the cells died and has subsequently been viably stored.

In some embodiments, a natural isolate or subculture of *Haematococcus* sp. KAU-01 is used and in others this strain may be further modified, mutated or genetically engineered.

A passaged or lab-adapted strain of *Haematococcus* sp. KAU-01 may differ from the natural isolate, for example, in rate of growth, nutrient preference, pH preference, temperature preference, hydrophobicity, hydrophilicity, or genetically or epigenetically. A modified strain may also produce more or less pigment, such as astaxanthin, carotenoids or other dyes or pigments, or biomass under otherwise similar culture conditions.

Modified versions of this species may have one or more coding sequences, genes or polypeptides with alterations, such as deletions, substitutions or insertions of nucleotides or amino acid residues. Generally, related strains will have genomic DNA or one or more ribosomal DNA genes 95, 96, 97, 96, 99, 99.5, 99.9, <100 or 100% identical or similar to that of *Haematococcus* sp. KAU-01. BLASTN may be used to identify a polynucleotide sequence having at least 70%, 75%, 80%, 85%, 87.5%, 90%, 92.5%, 95%, 97.5%, 98%, 99% or <100% sequence identity to a reference polynucleotide such as a polynucleotide encoding a collagen, one or more hydroxylases described herein, or signal, leader or secretion peptides or any other proteins disclosed herein. A representative BLASTN setting modified to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to hypertext transfer protocol secure://_blast.ncbi.nlm.nih.gov/Blast.cgi?PROGRAM= blastn&PAGE_TYPE=BlastSearch&LINK_LOC= blasthome (last accessed Aug. 10, 2020).

BLASTP can be used to identify an amino acid sequence having at least 70%, 75%, 80%, 85%, 87.5%, 90%, 92.5%, 95%, 97.5%, 98%, 99% or <100% sequence identity, or similarity to a reference amino acid, such as a collagen amino acid sequence, using a similarity matrix such as BLOSUM45, BLOSUM62 or BLOSUM80 where BLOSUM45 can be used for closely related sequences, BLOSUM62 for midrange sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at: hypertext transfer protocol secure:// blast.ncbi.nlm.nih.gov/Blast.cgi?PROGRAM= blastp&PAGE_TYPE=BlastSearch&LINK_LOC= blasthome (last accessed Aug. 10, 2020).

In some embodiments, *Haematococcus* sp. KAU-01 is further modified or mutated, for example, by chemical or radiological mutation or by genetic engineering and recombinant DNA techniques. Such modifications may be made to improve growth or biomass production under particular culture conditions, to protect it from contamination by other microorganisms, for example, by making it resistant to one or more antibiotics, or to improve its functional properties such as its growth rate or ability to produce higher densities of biomass under particular culture conditions, its ability to form or not form a biofilm, its ability to adhere or not adhere to a substrate such as plastic, glass, ceramic, or metal, or its ability to absorb light within a specific range of wavelengths, or to boost its ability to produce valuable biological materials, such as fatty acids or astaxanthin or hydrogen (hypertext transfer protocol secure://newatlas.com/algae-hydrogen-production-boost-tau/45831/). Such a modified microalga may also be mutated or engineered to prevent production of one or more of such biological materials that interfere with growth of the microalgae or production of biomass. Modifications include induction of auxotrophy for one or more molecules made by the unmodified strain or the incorporation of expression control sequences such as repressible promoters into the genome or episomes of the microalgae. A *Haematococcus* variant may have one or more epigenetic changes to its DNA, such as a variant methylation or hydroxymethylation pattern in its genomic DNA, a difference in histone methylation, or difference in microRNA expression, compared to an otherwise identical isolate. Epigenetic variants are those having a heritable phenotype change that does not involve alterations in its DNA sequence. In some alternate embodiments, a microalgae species other than a *Haematococcus* sp. may be cultured in AAHKAU medium including microorganisms such as *Chlorophyta, Pediastrum* sp. and *Scencedesmus* sp, The following examples illustrate various aspects of the present invention. They are not to be construed to limit the claims in any manner whatsoever.

Example 1

Culture of *Haematococcus* sp. KAU-01 with Normal Aeration and in Presence of Combustion Gases As shown herein the inventors have developed a culture medium and methods useful for convenient and economical large scale biomass production from microalgae that mitigates or eliminates atmospheric pollution caused by flue gases emissions from fossil fuel power plants while enhancing microalgae growth and biomass production.

Materials and methods. Three stock solutions, "A" for major nutrients, "B" for micronutrients and "C" for vitamins were prepared as described above. To produce a 1×AAHKAU culture medium as described in Table 1 approximately 1.0, 1.0 and 1.0 ml of stock solution of 'A', 'B" and 'C' were respectively diluted into 1 L of water. Two types of water used to prepare the culture medium, one was distilled water and another one was municipal water. After dilution of stock solutions, the water pH was checked which was about 3.0 and $Na_2CO_3$ was added to adjust the pH to pH 7.00 prior to inoculating the 1× medium with *Haematococcus* sp. KAU-01 for growth and biomass production. The study was carried out until all the motile cells turn to inactive cysts.

Three groups of culture experiments A, B and C were designed to identify the best culture conditions for with *Haematococcus* sp. KAU-01.

The cultures in Group A (A1, A2 and A3) were continuously aerated with normal air to agitate the cultures, those in Group B (B1, B2 and B3) were given 15% $CO_2$ gas periodically after day 4 of culture along with continuous normal aeration, and those in Group C (C1, C2 and C3) were given mixture gases (15% $CO_2$+5% CO+1% NO+1% $NO_2$) periodically after the fourth day of culture along with continuous normal aeration.

The A1 culture was done with adding of initial concentrations of stock solutions of AAHKAU medium (solution A, B and C of AAHKAU medium at 3.5, 1.0 and 1.0 ml/L).

Initial nutrients concentration of A2 medium was same as regards to the initial nutrients concentration of A1, and after four days of culture a continuous nutrients of AAHKAU medium was provided to the A2 culture. For that, initial concentrations of stock solutions of AAHAKU medium was diluted 2.5 times in distilled water. Thereafter, the diluted stock solutions were added continuously to maintain constant pH of 7.5, since stock solution of AAHAKU medium is highly acidic. The diluted AAHKAU medium was added with a pH controller and dosing pump (BL7916-2 pH Controller with Pump, Hanna, Instrument Co.)

The A3 culture was same as regards to A1 culture except exchange of 20% ongoing culture medium with fresh initial concentration of AAHKAU medium concentration after four days of culture. The exchange of culture medium was done on every third day.

In B1 culture, $CO_2$ gas was provided periodically after four days of culture to adjust the pH 7.5. $CO_2$ gas was provided to the culture during the light period to adjust pH of 7.5. The culture pH was checked hourly and $CO_2$ gas was provided to the culture.

The B2 culture was the same as the B1 culture except for addition of 2.5 times dilute, initial concentration of AAHKAU medium stock solutions to adjust pH of 7.5 once in a day after four days of culture while rest of the time the pH was adjusted 7.5 with periodically providing of $CO_2$ gas to the culture. $CO_2$ gas was provided following the same way as described in B1 culture.

The B3 culture was same as regards to B1 culture except exchange of 20% ongoing culture medium with fresh initial concentration of AAHKAU medium. The exchange of 20% ongoing culture medium of B3 was same as regards to A3 culture. And $CO_2$ gas was provided as described for the B1 culture.

In the C1 culture, the mixture gases ($CO_2$ 15%+CO 5%+NO 1%+$NO_2$ 1%+$N_2$ balance) was provided periodically after four days of culture to adjust the pH of 7.5. The mixture gases were provided following the same way as described for the B1 culture.

The C2 culture was same as the C1 culture except for addition of 2.5 times diluted stock solution of AAHKAU medium once in a day to adjust pH 7.5 after four days while the rest of the time pH was adjusted 7.5 with mixture gases. Periodically providing of mixture gases was same as described for the C1 culture.

The C3 culture was same as regards to C1 except exchange of 20% ongoing culture medium with fresh initial concentration of AAHKAU medium. The exchange of 20% medium was same as regards to A3 culture. Periodical providing of mixture gases was same as described for the C1 culture.

Exchange of culture medium in A3, B3 and C3 was done by discharging of 20% old culture medium through filtration and replacement of newly prepared culture medium (initial concentrations of nutrients). For exchanging, a 5.00 micron-mesh size filter bag (Zhengzhou Mining Machinery, Co. Ltd, China) was cut and sacks were made. Sacks were 15 cm long and 10 cm wide with a small opening where one side of clear flexible 4 mm air tube of 1.5 meter length was pushed inside of sacks and fixed with Gorilla super glue and cellophane. Then, one side of vein saline tube was pushed inside of the flexible tube and fixed tightly with cellophane and another part a regulator was kept to control the out flow of culture medium. Thereafter, the culture medium was allowed to discharge by gravitation force and flow speed was controlled by the regulator. The alga that attached to the sack's surface were removed by reverse forced air flow.

Culture medium exchange was stopped when 90% motile cells turned into cysts. The culture was grown in transparent 12 L NOVA bottles (Health Water Bottling Company, the Kingdom of Saudi Arabia, hypertext transfer protocol://worldwideweb.novawater.com/en/index.php).

The upper parts of the bottles were cut to form a cylindrical photobioreactor. Each bottle was filled up with 10 liters AAHKAU culture medium. The culture was grown at temperature of 25° C. under fluorescent lights (180 µE $m^{-2}$ $s^{-1}$) on a 14:10 h L:D light dark photo cycle for 26 days. All cultures were conducted in triplicate (n=3).

Determination of growth and biomass production. The growth of *Haematococcus* sp. KAU-01 was determined in two ways. One was direct cell counting and the other weighing dry biomass. Samples were collected from each flask every other day.

For dry biomass estimation, a 20 mL sample was collected from each culture flask, filtered through preweighed GF/F Whatman filter paper. A preweighed filter paper that was soaked in distilled water and dried at the same time was used as a blank. The biomass filter paper was kept at 55° C. in an oven, dried and weighed, and the dry weight biomass was calculated as g/L.

For determination of particulate materials, 250 mL discharge water was filtered and dried using filter paper following the same procedure used for biomass determination and expressed as mg/L.

For cell counting, a 5 mL sample was collected from each culture flask and fixed with 2% of Lugol's iodine solution. The fixed sample was dilute and the cells were counted using a S-R counting chamber under an inverted microscope.

A growth curve was plotted using the dry biomass and cell counting values. The specific growth rate ($\mu$), defined as the increase in cell density or dried biomass per unit time (Pirt 1975), was calculated and formulated as follows:

$$\mu = \mathrm{Ln}(X1/X0)/(t1-t2) \qquad (i)$$

where $X_0$ and $X_1$ are cell density/dried biomass at the beginning ($t_0$) and end ($t_1$) of a selected time interval between inoculation and maximum cell density dried biomass, respectively. For the growth curve of each sample, replicates were counted and the mean value used.

Microscopic study was done to evaluate the formation of palmella from vegetative cells (two equal flagella). The density of palmella was found to be 90% on the next sampling day of maximum specific growth in each culture.

In the A culture group, more than 90% of palmella were found to be formed on days 16, 18 and 20 of culture in A1, A2, and A3 culture, respectively.

In the B culture group, a similar amount of percentage of palmella found on 20, 22 and $24^{th}$ day of culture in 'B1, B2, and B3, respectively.

Figure 2:
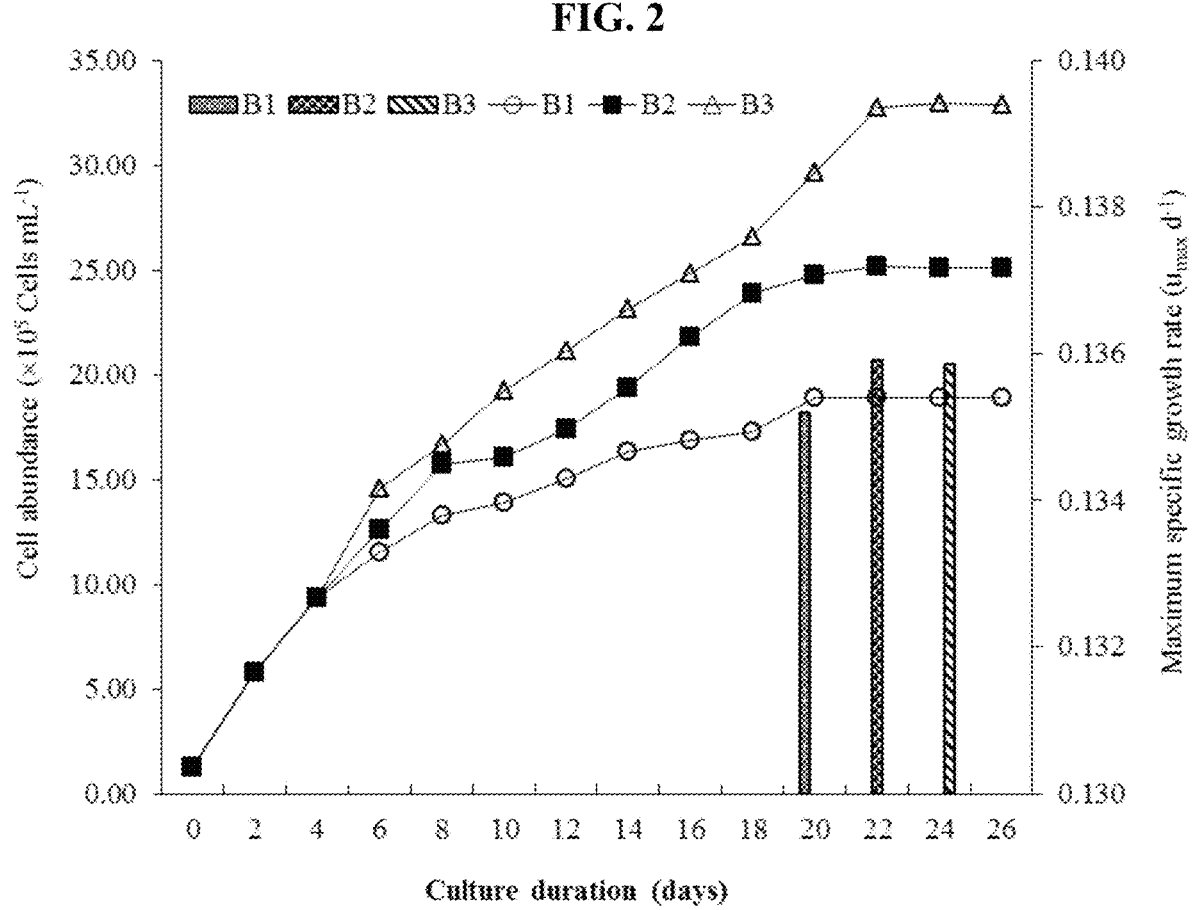
FIG. 2. Variation in maximum specific growth rate ($u_{max}$ $d^{-1}$) and growth curve with cell abundance ($\times 10^5$ cells $mL^{-1}$) of *Haematococcus* sp. KAU cultured in AAHKAU medium within 'B' culture group. B1 normal aeration+15% $CO_2$; B2: normal aeration+15% $CO_2$, pH maintained at pH 7.5 and additionally pH was maintained 7.5 by injecting of stock solution A and B on alternative day; B3: normal aeration+15% $CO_2$, 20% media replacement on alternate days.
Figure 3:
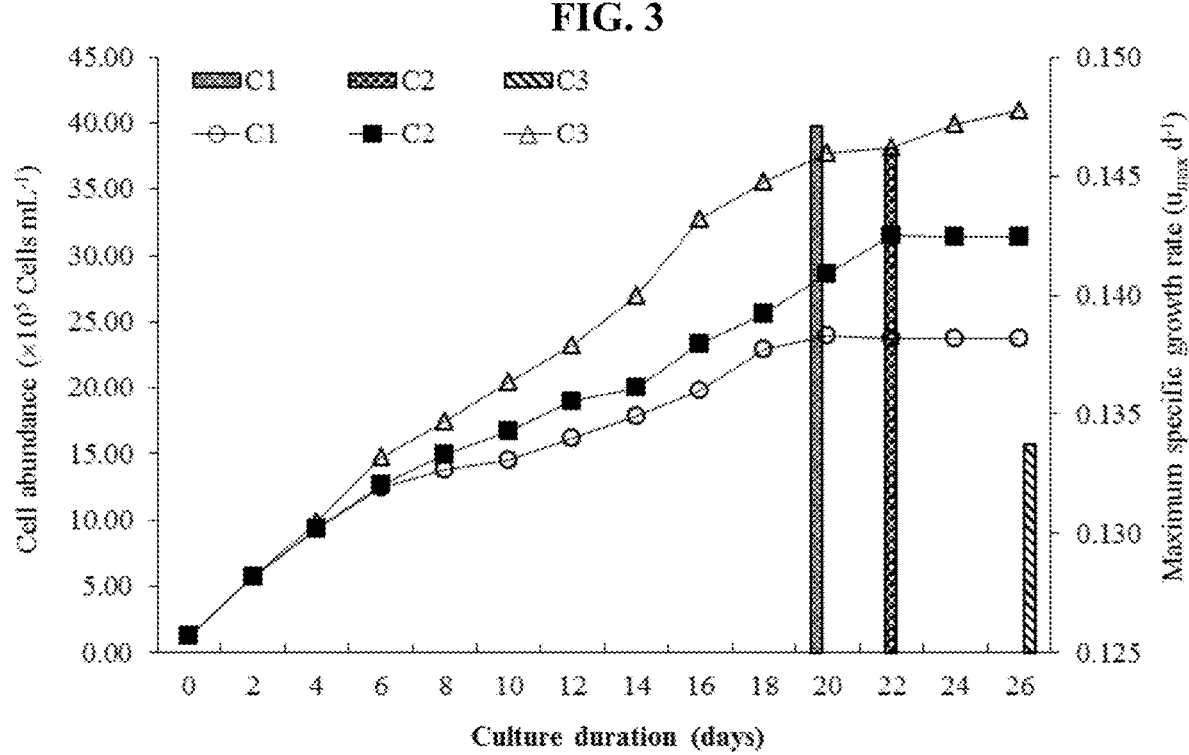
FIG. 3. Variation in maximum specific growth rate ($u_{max}$ $d^{-1}$) and growth curve with cell abundance ($\times 10^5$ cells $mL^{-1}$) of *Haematococcus* sp. KAU cultured in AAAHKAU medium within "C" culture group: C1 normal aeration+15% $CO_2$+CO 5%+NO 1%+$NO_2$ 1%+$N_2$ balance; C2: normal aeration+15% $CO_2$+CO 5%+NO 1%+$NO_2$ 1%+$N_2$ balance, pH maintained at pH 7.5, and additionally pH was maintained 7.5 by injecting of stock solutions A and B on alternate days; C3: normal aeration+15% $CO_2$+CO 5%+NO 1%+$NO_2$ 1%+$N_2$ balance, 20% media replacement on alternate days.

Similarly, in the C culture group, it was observed on 20, 24 and $26^{th}$ day of culture in C1, C2 and C3, respectively (FIGS. 1, 2 and 3).

Cell abundance and Biomass production. Maximum specific growth rate ($\mu_{max}$ d$^{-1}$) is an informative way to ascertain microbial activity which can increase at exponential rates. Growth characteristics determination under controlled conditions can play significant biological information for mass culture of *Haematococcus* sp.

The $\mu_{max}$ d$^{-1}$ of *Haematococcus* sp. KAU-01 varied from 0.138 to 0.157 (see bars in FIG. 1), 0.135 to 0.136 (see bars in FIG. 2) and 0.134 to 0.147 d$^{-1}$ (see bars in FIG. 3) in culture groups 'A', 'B', and 'C', respectively. Among all cultures, the highest $\mu_{max}$ d$^{-1}$ was in C1.

In the A culture group, the cell abundance varied from 15.45 to 25.93×10$^5$ cells mL$^{-1}$ with the highest in A3, followed by A2 and A1 (FIG. 1).

In the B group, the cell abundance varied from 18.90 to 32.97×10$^5$ cells mL$^{-1}$, and the highest was in B3, followed by B2 and B1 (FIG. 2).

Similarly, in the C group, the cell abundance varied from 23.98 to 40.92×10$^5$ cells mL$^{-1}$ with the highest in C3, followed by C2 and C1 (FIG. 3). However, among all nine cultures, C3 had the highest cell abundance of *Haematococcus* sp. KAU-01. Biomass production of *Haematococcus* sp. KAU-01 showed similar pattern as growth curve pattern of cell abundance.

Figure 4:
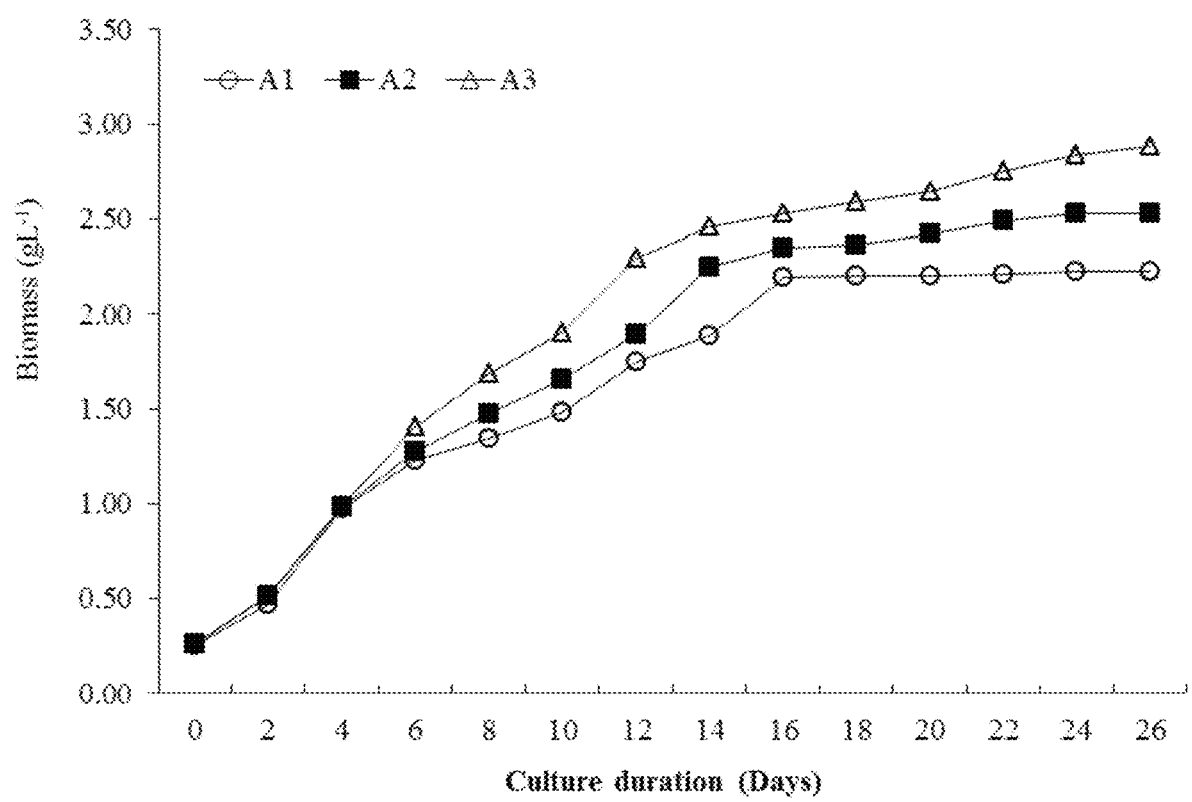
FIG. 4. Variation of biomass ($gL^{-1}$) production of *Haematococcus* sp. KAU cultured in AAHKAU medium in A culture group.

Biomass production was found to be varied from 2.19 to 2.89 gL$^{-1}$ and the highest was in A3, followed by A2 and A1 as shown by FIG. 4.

Figure 5:
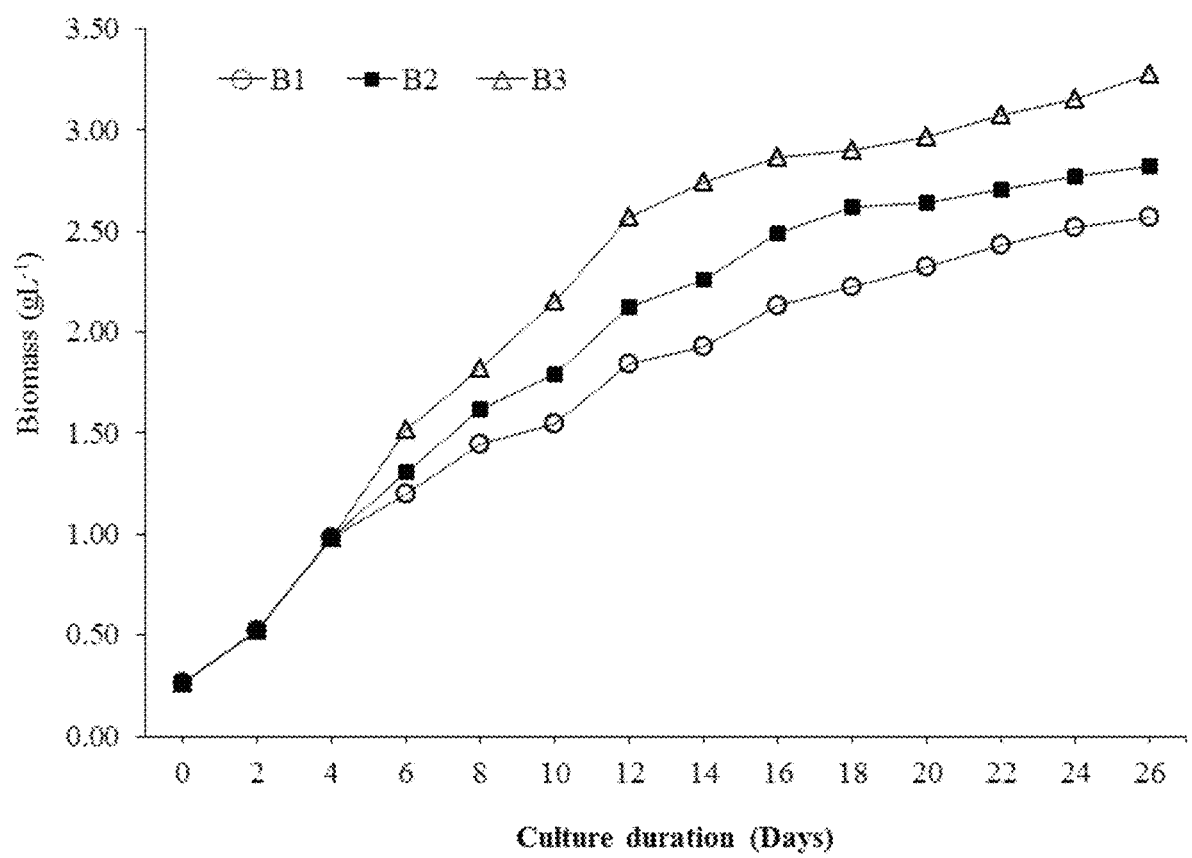
FIG. 5. Variation of biomass ($gL^{-1}$) production of *Haematococcus* sp. KAU cultured in AAHKAU medium in B culture group.

In the B group, the highest biomass production was 3.28 gL$^{-1}$ in B3 culture, followed by B2 (2.83 gL$^{-1}$) and B1 (2.57 gL$^{-1}$) as shown by FIG. 5.

Figure 6:
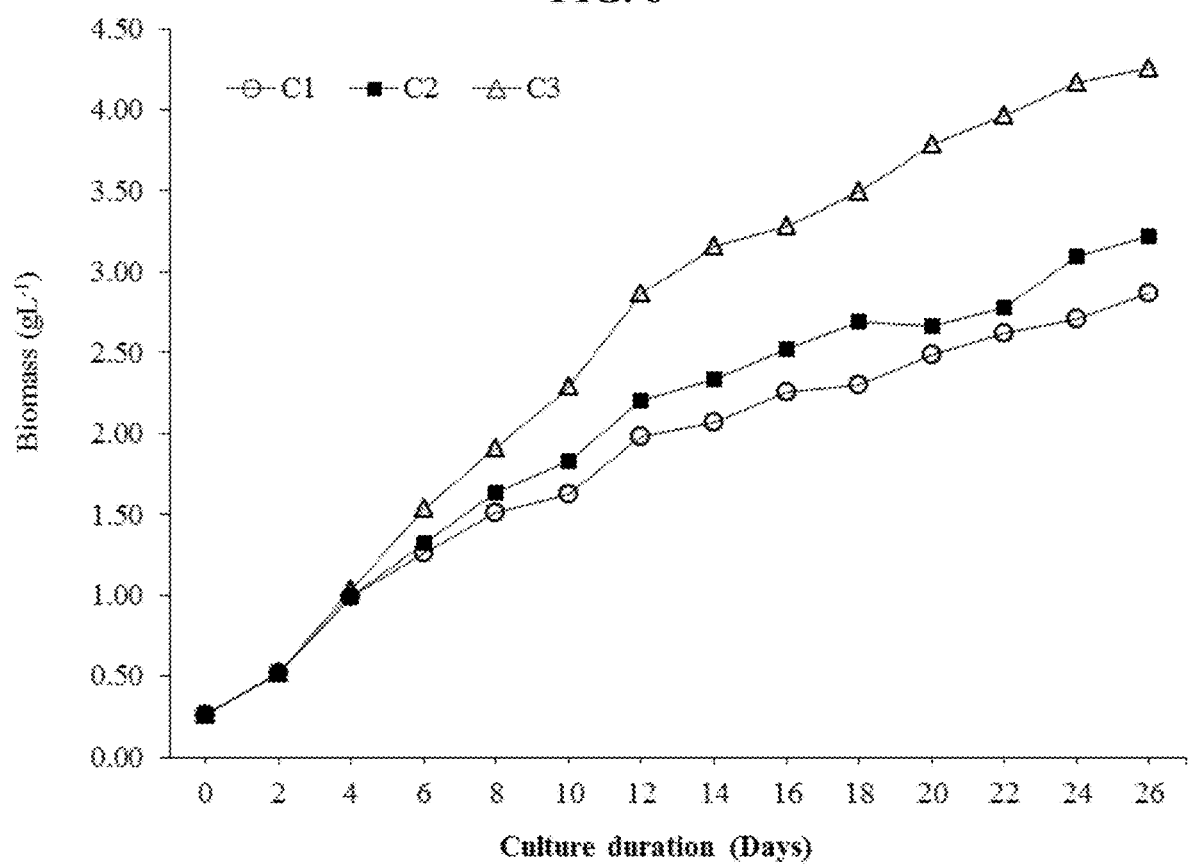
FIG. 6. Variation of biomass ($gL^{-1}$) production of *Haematococcus* sp. KAU cultured in AAHKAU medium in C culture group.

Similarly, in C group, the biomass production varied from 2.89 to 4.26 gL$^{-1}$ and the highest biomass production was found in C3 among C culture group (FIG. 6). However, the highest biomass production was found in C3 culture among the three culture groups.

Increased biomass production of B1, B2 and B3 of B group was 0.35, 0.30 and 0.90 gL$^{-1}$ higher than that the biomass production of A1, A2 and A3, respectively. The percentage calculation revealed that the biomass production of B1, B2 and B3 was 15.63, 11.68 and 37.90% more than that the biomass production of A1, A2 and A3, respectively.

Similarly, biomass production of C1, C2 and C3 group was 0.65, 0.69 and 1.89 gL$^{-1}$ higher than that the biomass production of A1, A2 and A3, respectively. A percentage calculation revealed that the biomass production of C1, C2 and C3 was 29.03, 27.32 and 79.97% more than that the biomass production of A1, A2 and A3, respectively.

In medium replacement cultures, the increased biomass production was 0.34 and 1.34 gL$^{-1}$ higher in B3 and C3 than that of the biomass production of A3, and it showed 11.71 and 45.79% high in B3 and C in comparison with A3; see Table 2A which shows the effects of culturing in the presence of air (A), $CO_2$ (B), or combustion gas mixture (C).

TABLE 2A

Comparison of biomass yields (g/L) for *Haematococcus* sp. KAU-01 under conditions A (air), B ($CO_2$) and C (combustion gas mixture).

| Increased in 'B' compared to 'A' | | | Increased in 'C' compared to 'A' | | | Increased in 'C' compared to 'B' | | | Increased biomass in medium replacement cultures A3, B3 and C3 | |
|---|---|---|---|---|---|---|---|---|---|---|
| B-Cul | gL$^{-1}$ | % | C-Cul | gL$^{-1}$ | % | C-Cul | gL$^{-1}$ | % | gL$^{-1}$ | % |
| B1 | 0.35 | 15.63 | C1 | 0.65 | 29.03 | C1 | 0.30 | 11.59 | B3-A3 0.34 | 11.71 |
| B2 | 0.30 | 11.68 | C2 | 0.69 | 27.32 | C2 | 0.40 | 14.00 | C3-A3 1.34 | 45.79 |
| B3 | 0.90 | 37.90 | C3 | 1.89 | 79.97 | C3 | 1.30 | 39.59 | | |

TABLE 2B

Difference of biomass production gram per liter (gL$^{-1}$) and percentage (%)during the culture of *Haematococcus* sp. KAU-01 under different culture conditions A1, A2 or A3; B1, B2 or B3; or C1, C2 and C3.

| | Difference of Biomass production (gL$^{-1}$) | Difference of Biomass production in percentage (%) | |
|---|---|---|---|
| Different Cultures | gL$^{-1}$ | Percent calculation | % |
| (A2 – A1) | 0.31 | {(A2 – A1)/A1} × 100 | 13.77 |
| (A3 – A1) | 0.66 | {(A3 – A1)/A1} × 100 | 29.82 |
| (A3 – A2) | 0.36 | {(A3 – A2)/A2} × 100 | 14.10 |
| (B2 – B1) | 0.25 | {(B2 – B1)/B1} × 100 | 9.89 |
| (B3 – B1) | 0.71 | {(B3 – B1)/A1} × 100 | 27.50 |
| (B3 – B2) | 0.45 | {(B3 – B2)/B2} × 100 | 16.02 |
| (C2 – C1) | 0.35 | {(C2 – C1)/C1} × 100 | 12.27 |
| (C3 – C1) | 1.17 | {(C3 – C1)/C1} × 100 | 59.49 |
| (C3 – C2) | 1.35 | {(C3 – C2)/C1} × 100 | 42.06 |

Table 2B shows the difference of biomass production gram per liter ($gL^{-1}$) and percentage (%) within each of the A, B and C groups thus showing the effects of different culture conditions 1, 2 or 3 on biomass production. Increased biomass production was observed in A2 and A3 which was 0.31 and 0.66 $gL^{-1}$, and it was 13.77 and 29.82% when compared with the biomass production of A1. In A3, the biomass production was 0.36 $gL^{-1}$ and 14.10% higher than that of the biomass production of A2. Similarly, in B2 and B3 the biomass production was 0.71 and 0.45 $gL^{-1}$ more in comparison with the biomass production of B1, and it was 9.89 and 27.50% than that of B1. Biomass production of B3 was 0.45 $gL^{-1}$ and 16.02% than that of the biomass production of B2.

In the C culture group, the biomass production 1.17 and 1.35 $gL^{-1}$ was higher in C2 and C3, respectively, in comparison with the biomass of C1, and it was 12.27 and 59.49% when compared with the biomass production of C1. Similarly, biomass production in C3 was 1.35 $gL^{-1}$ than that of the biomass production of C2, and it was 42.06% higher when compared with the biomass production of C2; see Table 2B.

Effects of Replacement of Culture Liquids.

Figure 7:
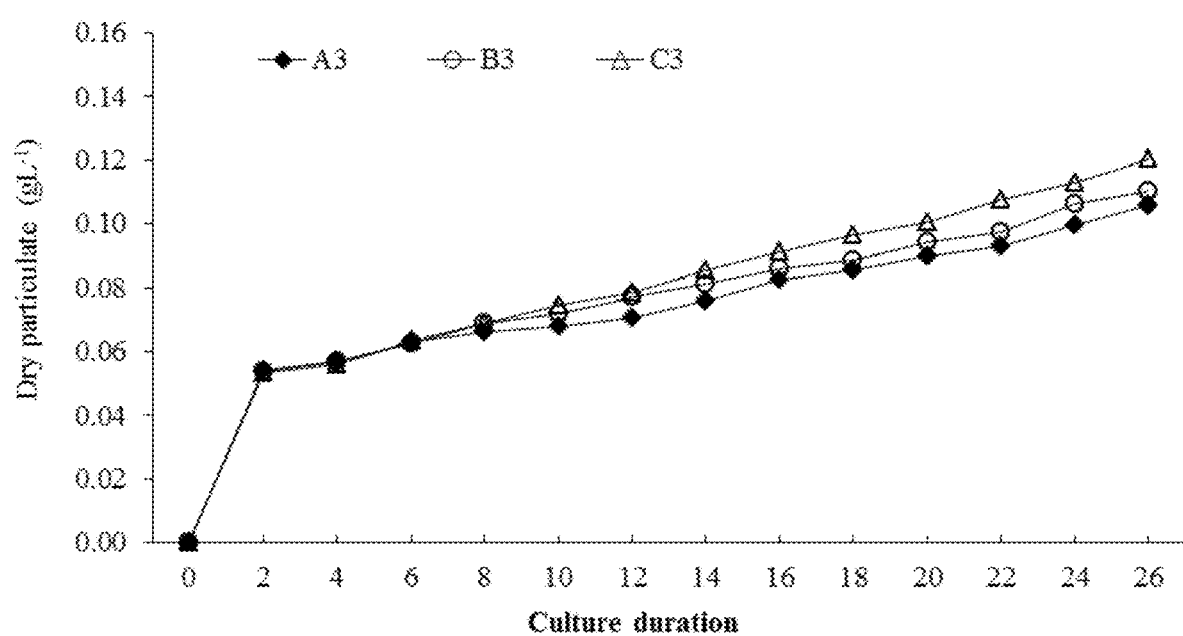
FIG. 7. Amount of dry particulate matter (cellular debris) from broken cells and cell walls during culture of *Haematococcus* sp. KAU in culture subgroups A3, B3 and C3 in which 20% of culture medium was replaced on alternate days after day 4 of culture.
Figure 11A:
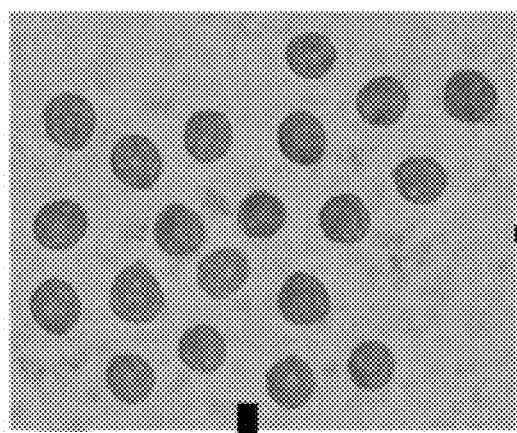
FIG. 11A depicts flagellated cells of *Haematococcus* sp. KAU-01.
Figure 11B:
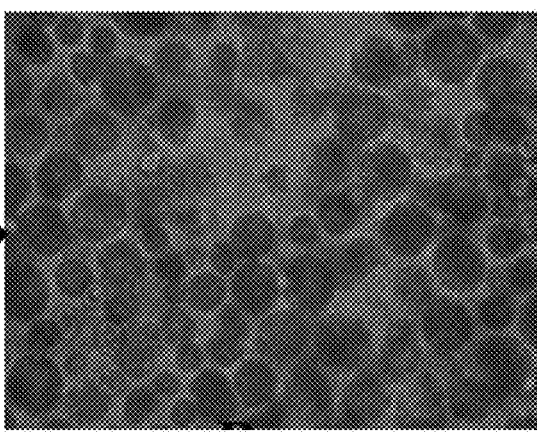
FIG. 11B shows cell walls broken or lysed due to lack of Ca-salts.
Figure 11C:
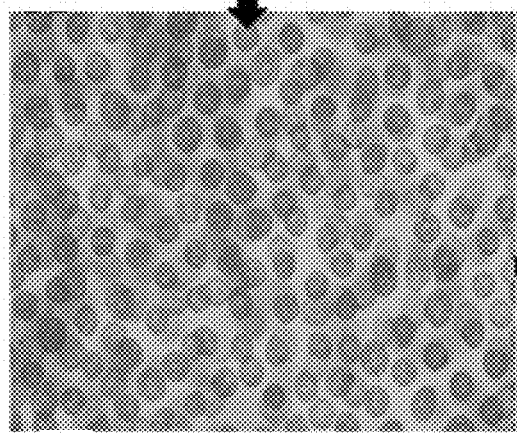
FIG. 11C shows cells without breaking of cell wall after gradually increasing Ca-salt concentration to 25.00 $mgL^{-1}$.
Figure 11D:
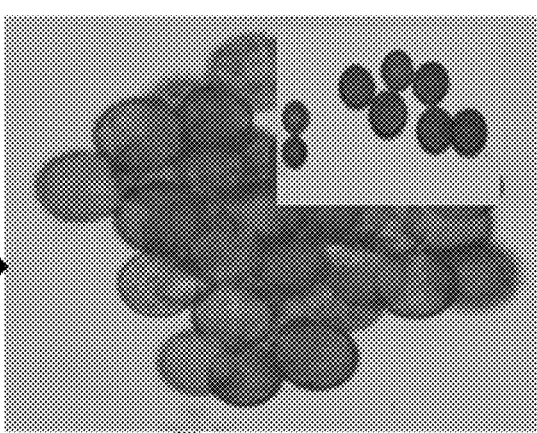
FIG. 11D depicts red cysts without lysis of cell.

The effects of replacement of liquid in the culture to reduce concentrations of cell debris, such as broken cells or cell walls, which can act as autoinhibitors of growth, were investigated. Soon after replacement, the culture medium, the discharged old culture medium was filtered following the same methods used to estimate cell biomass. The concentration of debris was 0.106, 0.110 and 0.120 $gL^{-1}$ in A3, B3 and C3, respectively, at the end of the study; FIG. 7.

Cultures of *Haematococcus* sp. KAU-01 made using batch, fed batch, and culture medium replacement were done with normal aeration, $CO_2$ and mixture gases supplying in certain interval along with normal aeration to maximize cell productivity and ultimately to obtain higher biomass production.

In all culture conditions *Haematococcus* sp. KAU-01 grew well but produced different cell abundances and quantities of biomass. The increasing of cell abundance was arrested soon after stationary phase when above 90% free moving cells turned into cysts or palmella.

In batch cultures having only normal aeration and/or $CO_2$ and gas mixtures supplied along with normal aeration cultures, cysts were observed earlier than in fed batch cultures and in culture medium replacement cultures.

In batch culture with normal aeration (A1) and with supply of $CO_2$ (B1) and mixture gases (C1), the cyst formation observed on $16^{th}$ and $20^{th}$ day of culture, respectively.

In fed batch culture with normal aeration (A2) and with supply of $CO_2$ (B2) and mixture gases (C2), the cyst formation was observed on $22^{th}$ day of culture, respectively.

In replacement culture system, the cyst formation was observed on 20, 22 and $24^{th}$ day of culture in A3, B3 and C3, respectively.

However, in replacement of culture system, the formation of palmella or cysts took longer time with normal aeration than that of the batch and fed batch cultures. Cyst formation took longest time in C3 culture, followed by B3 culture where mixture gases and $CO_2$ were supplied along with normal after replacement of culture medium. Here, the cyst formation time was longer those reported by Kaewpintong et al. who found formation of palmella from flagellated vegetative cell after $13^{th}$ day of cultivation in M1, F1 and Hong Kong media at high-density cultivation of vegetative cells of *H. pluvialis* in airlift bioreactor; Kaewpintong et al., *Photoautotrophic high-density cultivation of vegetative cells of Haematococcus pluvialis in airlift bioreactor*, BIORESOURCE TECHNOLOGY, January 2007, 98(2): 288-295.

Culture of *H. pluvialis* in different culture media and light intensities also showed a stationary phase between 10 to 12 days which was much lower than the inventors' culture systems; Imamoglu, E., et al. *Effect of Different Culture Media and Light Intensities on Growth of Haematococcus pluvialis*. INTERNATIONAL JOURNAL OF NATURAL AND ENGINEERING SCIENCES, 2007, 3, 05-09. Medium replacement cultures supplied with $CO_2$ and gas mixtures showed almost double capacity to form cysts than that of cyst formation than in the culture study of Kaewpintong et al., supra and Imamoglu, E., et al., supra.

Cell growth generally occurs when vegetative cells are flagellated. In palmella (cysts) the cells convert to an inactive form and cease further cell division. These results show that culture medium and conditions were quite suitable and facilitated cell division for a long time, thus ultimately increasing of cell abundance and biomass production. Moreover, it showed that replacement of culture medium with supplying of $CO_2$ and mixture gases along with normal aeration provided a higher efficiency to facilitate more cell division by providing suitable conditions for long time than in batch and fed batch culture systems.

Cell abundance and Biomass production. The inventors sought to acquire biological information, such as growth characteristics of *Haematococcus* sp. KAU-01 to discover mass culture to construct a high-density mass culture system. The $\mu_{max}d^{-1}$ was significantly ($p<0.05$) higher in 'C' culture group than that of the $\mu_{max}d^{-1}$ of 'A' and 'B' culture group, except for 'A1" culture, where the maximum cell growth and stationary phase were appeared about a week before than all other cultures. The $\mu_{max}d^{-1}$ in all cultures of this study was low in comparison with the study of Kaewpintong et al., supra who found $\mu_{max}d^{-1}$ of 0.21 $d^{-1}$ in F1 culture medium on $8^{th}$ day of culture. Tjahjono et al. found the maximum specific growth rate of *H. pluvialis* was about 0.25 $d^{-1}$ using basal growth medium grown in mixotrophic condition with sodium acetate as a carbon source on $3^{rd}$ day of culture; Tjahjono et al., *Hyper-accumulation of astaxanthin in a green alga Haematococcus pluvialis at elevated temperatures*, BIOTECHNOLOGY LETTERS. 1994, 16:133-138.

The $\mu_{max}d^{-1}$ can vary from culture to culture as well as initial cell abundance and occurrence of maximum cells abundance. However, the cell abundance was significantly higher ($p<0.05$) in all medium replacement cultures, followed by fed batch culture and batch culture. In batch culture with supplying of normal aeration, periodic supply of $CO_2$ and mixture gases along with normal aeration, the maximum cell abundance was $15.54 \times 10^5$, $18.90 \times 10^5$ and $23.98 \times 10^5$ cells $mL^{-1}$ in A1, B1 and C1 cultures, respectively (FIGS. 1, 2 & 3). Within batch culture, supply of mixture gases, $CO_2$ and normal aeration also showed significant ($p<0.05$) difference in cell abundance occurrence.

The cells abundance of batch cultures of normal aeration and supplying mixture gases, $CO_2$ along with normal aeration showed almost two to three folds higher than that of the results of obtained by Imamoglu et al., supra who reported that the maximum cell abundance occurred $7.75 \times 10^5$ and $8.10 \times 10^5$ cells $mL^{-1}$ in BG11 and RM culture media, respectively under the light intensity of 50 µmol photons $m^{-2}$ $s^{-1}$ and in RM medium, the recorded cell abundance was $9.50 \times 10^5$ cells $mL^{-1}$ when culture under 40 µmol photons $m^{-2}$ $s^{-1}$.

In fed batch cultures, the maximum cell abundance was $19.95 \times 10^5$, $25.17 \times 10^5$ and $31.50 \times 10^5$ cells $mL^{-1}$ in A2, B2, and C2 cultures, respectively (FIGS. 1, 2 and 3). Within fed batch cultures, the occurrence of cell abundance was also significantly difference, especially cell abundance in C2 was significantly ($p<0.05$) higher than that of B2, followed by A2 culture. Kaewpintong et al. studied high-density cultivation of vegetative cells of *H. pluvialis* in airlift bioreactor with supplying $CO_2$ and attained the maximum cell abundance $46 \times 10^4$ and $79.5 \times 10^4$ cells $mL^{-1}$, which is much lower than that of the cell abundance of the batch culture disclosed herein with periodic supplying of $CO_2$ and mixture gases as well as fed batch culture with supplying of $CO_2$ and mixture gases. The cell abundance was higher in all batch cultures in comparison with the above mentioned previous study.

This is consistent with the AAHKAU medium creating favorable circumstances for the higher growth of *Haematococcus* sp. KAU-01 in batch and fed batch culture with normal aeration or with periodic supply of $CO_2$ and mixture gases along with normal aeration. Cultures supplied with mixture gases showed more cell abundance than all other cultures. Moreover, the remarkable maximum cell abundance occurrence was found in a 20% replacement culture medium. The cell abundance was $25.93 \times 10^5$, $32.97 \times 10^5$ and $40.92 \times 10^5$ cells $mL^{-1}$ in culture of 'A3, B3, and C3, respectively (FIGS. 1, 2 & 3.). The cell abundance occurrence results in the medium replacement culture was much higher than those reported by Hata, N., et al., *Production of astaxanthin by Haematococcus pluvialis in a sequential heterotrophic-photoautotrophic culture*. JOURNAL OF APPLIED PHYCOLOGY. 2001, 13, 395-402.

Biomass production. Biomass production was found to be high in all media replacement cultures. The $1^{st}$ highest was 4.26 $gL^{-1}$ in C3 culture where mixture gases was supplied along with normal aeration, and the $2^{nd}$ highest was in B3 culture where $CO_2$ gas was supply in same way to the medium replacement culture. This biomass production was higher in comparison with the biomass production of *H. lacustris* culture in $NH_4Cl$ enriched medium with supply of 2% $CO_2$ as bubbles, where the biomass production was 3.74 $gL^{-1}$.

Higher biomass production in $CO_2$ and mixture gases supplying cultures confirmed that $CO_2$ and mixtures gases were converted to algal biomass by increasing the components for photosynthesis.

It was also found that the biomass production in cultures supplied with mixture gases showed more biomass production than that of the biomass production by only supplying $CO_2$. Mixture gases which are similar to flue gases (greenhouse gases) can be added as a gas or in bicarbonate form as cultivated microalgae grow too fast to be able to take sufficient flue gases from the water. Compressed air can be blended and provided for algal photosynthesis. Therefore, high valued microalgae can be grown in high cell density for $CO_2$ sequestration from flue gases, which ultimately reduces the emission of flue gases from fossil fuel-fired power plants.

These results demonstrate the remarkable growth of a commercially valuable microalgae *Haematococcus* sp. KAU-01 in newly formulated AAHKAU culture medium with normal aeration as well as in cultures having a periodic supply of $CO_2$ and/or mixture gases along with normal aeration. Superior results were obtained by replacement of culture medium to remove microalga autoinhibitors from ongoing cultures. This technology can be used for profitable, large scale biomass production while simultaneously controlling undesirable emissions of flue gases from the fossil fuel power plants.

Example 2

Isolation of *Haematococcus* sp. KAU-01. A sample was from Jeddah green valley where the water accumulates from several different mountains using a phytoplankton net with mesh size 10 micron. The sampling location was situated between 21° 36'71"N and 39° 43'16"E to 21° 32'75"N and 39° 28'89"E; see FIGS. 8A-8D. Ten liters of water was filtered using phytoplankton net and concentrated to 500 mL. Water samples were collected from 10 locations. The concentrated sample was mixed with 10 L of NOVA water (Saudi Arabian Nova Water—Health Water Bottling Co. Ltd.) enriched with F/2 medium stock solution (Aquacenter Inc., Leland, Mich., USA). One mL of A and B solution was added with 10 liter of NOVA water to grow microalgae which were grown in the transparent NOVA bottles. The culture was grown under 12:12 hrs light: dark (L: D) cycles at 120 µmol photons $m^{-2}s^{-1}$ ($\mu E\ m^{-2}\ s^{-1}$) and at temperature of 25° C. with moderate aeration for 5 days. A one mL sample was taken into S-R chamber from each culture and checked separately under light microscope.

A variety of different microalgae were observed including those of *Haematococcus* sp., *Scenedesmus* sp., *Pediastrum* sp., *Chlamydomonas* sp., *Nostoc* sp, and other diatoms found in wild culture samples. After checking the cultures were kept without aeration for one day to form thin layer scum at the surface water.

When light was provided on the top of culture bottles it was observed that *Haematococcus* formed thin layer scum at the surface of water if the water was not mixed or agitated. A thin layer was observed at the surface of the culture.

Tissue paper was applied to collect the microalgae from the surface. The wet tissue paper was transferred to new culture bottle and the culture was grown as described above. After 5 days, the culture turned green as observed by naked eyes. Then, a 1 mL sample was taken into S-R chamber and microscopically observed. Many motile *Haematococcus* and few *Chlamydomonas* sp., microalgae cells were seen.

A single isolate of *Haematococcus* sp. was recovered using the method described and incorporated by reference to Affan, A., et al., *Growth characteristics, biochemical composition and antioxidant activities of benthic diatom Grammatophora marina from Jeju coast, Korea*. ALGAE, 2006, 21, 141-48. Briefly, 1 mL of the mixed culture sample was diluted with 10 mL distilled water. Then, a 1 mL diluted sample was transferred to a Sedgwick Rafter (S-R) counting chamber, and single cell of *Haematococcus* was picked up with mouth aspirated micropipette (MSM) which was made by heating the tip of a glass Pasteur pipette and then drawing it to form a syringe type needle. The transparent PVC tube was pushed inside of the holder part of glass pasture pipette and finally the joint between glass pasture pipette and PVC tube was made air tight with vacuum latex tube. The length of the PVC tube was kept 75 cm which was convenient and comfortable to hold the tube into mouth and move the glass pasture pipette needle on the S-R chamber or into the multi-well for picking up the single cells. The needle of MSM was placed close to the target a single cell which was observed under an inverted microscope (Olympus IX71) and gently aspirated to isolate the cell inside of the MSM.

Thereafter, each single cell was transferred to a multi-well plate for subculture in culture medium which was prepared in distilled water enriched with F/2 medium and autoclaved. The isolation process was continued until a mono specie was obtained. The mono species was then streaked onto an agar plate with 2% agar (w/v) and two mL/L of "A" and "B"

stock solution F/2 and autoclaved distilled water. After two weeks, several green colonies were found in the agar plate.

A single colony from each plated was taken and put in plant tissue multi-culture well plate which was filled with 7.5 mL F/2 enriched distilled water culture medium. Thereafter, each well of multi well was observed under microscope to make sure that the isolated would be single species. The agar plating and liquid culture were continued until obtaining the single species of *Haematococcus* sp. Five mL of an aqueous culture of a single species (or isolate) of *Haematococcus* were poured and mixed in flask which was filled with F/2 enriched agar medium at temperature of 35° C. when the agar was still semi-liquid. This procedure resulted in the isolation of a mono species of *Haematococcus* which was designated *Haematococcus* sp. KAU-01.

Morphological and growth study in different reported media. The isolated microalga *Haematococcus* sp. KAU-01 was examined under a light microscope (LM, Eclipse 80i; Nikon Co.). Images were obtained using a camera (DXM 1200C; Nikon Co.). At first motile cells were observed discover the similarities or differences of their morphological characteristics with reported taxonomical characteristics. Then, life cycle study was conducted and images were taken using same microscope as mentioned above. After that, growth and biomass production study were conducted in various culture media.

1$^{st}$ step of culture in different culture media. The monostrain *Haematococcus* sp. KAU-01, was cultured in BG11 and other media described in Table 3. The chemical composition and concentration of different culture media (1×) used for growing *Haematococcus* sp. KAU-01 is shown in Table 3.

TABLE 3

Nutrient composition and concentration (mg/L) of different culture media for *Haematococcus* sp. 01.

| Ingredient | BG11 mg/L | MBG11 mg/L | OHM mg/L | Basal mg/L | RM mg/L | HK mg/L | MCM mg/L |
|---|---|---|---|---|---|---|---|
| $HNO_3$ | | | | | | | |
| $NaNO_3$ | 1500 | 1500 | | | 300 | | |
| $KNO_3$ | | | 410 | | | 300 | 200 |
| $K_2HPO_4$ | 40 | 320 | | | 80 | | 20 |
| $KH_2PO_4$ | | | | 150 | 20 | | |
| $Na_2HPO_4$ | | | 30 | | | 30 | |
| $NaH_2PO_4$ | | | | | | 35.5 | |
| $H_3PO_4$ | | | | | | | |
| $Ca(NO_3)_2 \cdot 4H_2O$ | | | | 100 | | | |
| $CaCl_2 \cdot 2H_2O$ | 36 | 36 | 110 | | 58.5 | 73 | 80 |
| $MgSO_4 \cdot 7H_2O$ | 75 | 200 | 246 | 40 | 10 | 24.6 | 100 |
| $Mg(NO_3)_2 \cdot 6H_2O$ | | | | | | | |
| $Na_2CO_3$ | 20 | 100 | | | | | |
| NaCl | | | | | 20 | | |
| Urea | | | | | | | |
| β-$Na_2$glycero phosphate | | | | 50 | | | |
| Citric acid | 6 | 6 | | | | | |
| $(NH_4)_5[Fe(C_6H_4O_7)]_2$ | 6 | 6 | | | | | |
| EDTA-$Na_2$ | 1 | 1 | | 2.71 | | 6.7 | |
| EDTA | | | | | 7.5 | | 0.0198 |
| Vitamin B12 | | | 0.0015 | 0.0001 | | | 0.004 |
| Biotin | | | 0.025 | 0.0001 | | | |
| Thiamine HCl | | | | 0.01 | | | |
| Thiamine | | | | 0.0175 | | | |
| $H_3BO_3$ | 286 | 286 | | | 0.3 | 0.003 | 61 |
| $MnCl_2 \cdot 4H_2O$ | 1.81 | 1.81 | 0.98 | 0.108 | | | 4.1 |
| $MnSO_4 \cdot H_2O$ | | | | | 1.5 | 0.001 | |
| $ZnSO_4 \cdot 7H_2O$ | 0.22 | 0.22 | | 0.066 | 0.1 | 0.014 | 4.1 |
| $Na_2MoO_4 \cdot 2H_2O$ | 0.39 | 0.39 | 12.0 | 0.0075 | | 0.001 | |
| $(NH_4)_6Mo_7O_{24} \cdot 4H_2O$ | | | | | 0.3 | | 38.0 |
| $CuSO_4 \cdot 5H_2O$ | 0.08 | 0.08 | 0.012 | | 0.08 | 0.012 | 6.0 |
| $Co(NO_3)_2 \cdot 6H_2O$ | 0.05 | 0.05 | | | 0.26 | | |
| $FeCl_3 \cdot 6H_2O$ | | | | 5.888 | | | 0.0244 |
| $FeSO_4 \cdot 7H_2O$ | | | | | | 8.3 | |
| $CoCl_2 \cdot 6H_2O$ | | | 0.11 | 0.12 | | 0.0005 | 5.1 |
| Trisaminomethane | | | | 500 | | | |
| Fe(III)citrate$H_2O$ | | | 2.67 | | | | |
| $Cr_2O_3$ | | | 0.075 | | | | |
| $SeO_2$ | | | 0.005 | | | | |

Media were made with the respective amounts of chemical ingredients described above, diluted in distilled water and then autoclaved for 15 mins. A 1.5 liter medium was made for each of culture media recipes. Each culture was grown in one liter Erlenmeyer Flask with 500 mL of each culture medium at temperature of 25° C. under fluorescent lights (120 µE m$^{-2}$ s$^{-1}$) on a 12:12 h L:D photo cycle with moderate aeration for 16 days. All cultures were conducted in triplicate (n=3).

Determination of growth and biomass production. Growth of *Haematococcus* sp. KAU-01 was determined in two ways, one was direct cell counting and another weighing dry biomass. Samples were collected from each flask every other day. For dry biomass estimation, a 20-mL sample was collected from each culture flask, filtered through preweighed GF/F Whatman filter paper. A preweighed filter paper that was soaked in distilled water and dried at the same time was used as a blank. The biomass filter paper was kept at 55° C. in an oven, dried and weighed, and the dry weight biomass was calculated as $gL^{-1}$. For cell counting, a 5-mL sample was collected from each culture flask and fixed with 2% of Lugol's iodine solution. The fixed sample was diluted and the cells were counted using a S-R counting chamber under an inverted microscope. Dry biomass and cell counting values were used for plotting as a growth curve.

The specific growth rate ($\mu$), defined as the increase in cell density or dried biomass per unit time was calculated and formulated as follows:

$$\mu = \frac{\ln(X_1/X_0)}{t_1 - t_0}$$

where $X_0$ and $X_1$ are cell density/dried biomass at the beginning ($t_0$) and end ($t_1$) of a selected time interval between inoculation and maximum cell density dried biomass, respectively. For determining the growth curve of each sample, replicates were counted and the mean value was used.

Preparation of *Haematococcus* sp. KAU-01-culture medium. The condition and biomass production of *Haematococcus* sp. KAU was dependent on the medium they were cultured in. This may be related with different chemicals with different concentrations in above mentioned different cultures media. Some cells lysed during culture in different media and the biomass production was gradually decreasing. Based on these observations, the inventors sought to increase biomass production by providing media and conditions that would keep cells in a motile division state and that would subsequently increase biomass production in a cyst state which is important for industrial scale production of biomass.

The inventors observed that there were more lysed cells in culture media which were prepared without calcium, that cells were weak and plate rather than dark green when a culture medium has a low concentration of magnesium, and that a high concentration of $Ca(NO_3)_2$ arrested culture growth and caused milky turbidity at a pH above 8.50.

Another coincident negative effect microscopically observed in these cultures was that normal, motile swimming mode was disrupted resulting in slow moving or stationary cells when cellular debris aggregated to the flagella and periphery of the transparent cell walls.

Consequently, the inventors developed new culture media that avoided or ameliorated these problems, for example, by gradually adding or titrating Ca and Mg salts such as $Ca(NO_3)_2$ and $Mg(NO_3)_2 \cdot 6H_2O$ to select a concentration of Ca and Mg that did not negatively impact cell growth and biomass production. These may be slightly higher when water containing Ca and Mg is used to produce the medium. Preferably, the above concentrations of Ca and Mg do not vary by more than ±1, 2, 3, 4, 5, 10, 15 or 20% in modified forms of AAHKAU medium and preferably, any added Ca and Mg is added as a nitrate salt.

Media stock solutions containing major nutrients such as major nutrients $NaNO_3$, $KNO_3$, $Ca(NO_3)_2$, $Mg(NO_3)_2 \cdot 6H_2O$, $K_2SO_4$, $K_2HPO_4$, $KH_2PO_4$, $MgSO_4 \cdot 7H_2O$, urea, $HNO_3$, and $H_3PO_4$; and as micro nutrients $FeCl_3 \cdot 6H_2O$, $H_3BO_3$, $Co(NO_3)_2 \cdot 6H_2O$, $K_2Cr_2O_7$, $CuSO_4 \cdot 5H_2O$, $MnSO_4 \cdot H_2O$, $ZnSO_4 \cdot 6H_2O$, $Na_2$-ETDA, and HCl were formulated as disclosed below. For the vitamin solution, thiamine, +D-biotin, and cyanocobalamin were diluted in autoclaved distilled water and during culture 100 µl/L the vitamin stock solution was added in one liter of culture medium.

$2^{nd}$ step of culture to select best culture media. Three stock solutions were prepared, major nutrients ("A"), micronutrients ("B") and vitamins ("C"). Distilled water, filtered natural seawater and autoclaved distilled water was used to make stock solution of "A", "B", and "C", respectively. Then, five concentrations of "A", five concentrations of "B" and a one concentration of "C" stock solutions were added to freshwater to culture of *Haematococcus* sp KAU.

The chemical concentrations of stock solution "A" were $NaNO_3$ (375.00 g), $KNO_3$ (75.00), $Ca(NO_3)_2$ (25.00 g), $Mg(NO_3)_2 \cdot 6H_2O$ (55.00 g), $K_2HPO_4$ (45.00 g), $KH_2PO_4$ (40.00 g), $K_2SO_4$ (10.00 g), $MgSO_4 \cdot 7H_2O$ (23.75 g), urea (1.75 g), $HNO_3$ (65.00 ml/L) and $H_3PO_4$ (15 ml/L) which were diluted in autoclaved distilled water and the final volume was made 1 L.

For stock solution "B", $FeCl_3 \cdot 6H_2O$ (35.00 g), $H_3BO_3$ (10.00 g), $Co(NO_3)_2 \cdot 6H_2O$ (2.50 g), $K_2Cr_2O_7$ (1.00 g), $CuSO_4 \cdot 5H_2O$ (1.00 g), $MnSO_4 \cdot H_2O$ (2.50 g) $ZnSO_4 \cdot 6H_2O$ (7.50 g), $(NH_4)_6Mo_7O_{24} \cdot 4H_2O$ (2.50 g), $Na_2$-ETDA (10.00 g) and HCl (10.00 ml) were diluted in filtered natural seawater and finally the volume was made 1 L. For stock solution "C", thiamine (10.00 g), +D-biotin (0.03 g) and cyanocobalamin (0.001 g) were diluted in autoclaved distilled water and finally the volume was made 1 L.

Thereafter, 5 concentrations of "A", "B" and one concentration of "C" were diluted for making culture medium to test growth of *Haematococcus* KAU sp. The diluted concentration of "A" stock solution was 0.5, 0.75, 1.00, 1.25 and 1.50 ml/L to prepare 'A1', 'A2', 'A3', 'A4' and 'A5' culture medium, respectively. Similarly, the diluted concentration of "B" stock solution was 50.00, 75.00, 100.00, 125.00 and 150.00 µl/L in 'A1', 'A2', 'A3', 'A4' and 'A5' culture medium, respectively. The stock solution "C" was added 100.00 µl/L in 'A1', 'A2', 'A3', 'A4' and 'A5' culture medium, respectively. The chemical concentration given in Table 1, is the final concentration for culture medium and the concentration unit is mg/L for salts and µl/L for acids. In Tables 4A and 4B, the concentrations of chemicals are given in mg/L and µl/L.

Tables 4A-4C shows ingredients in each major (A1-A5) and micro stock solution (B1-B5) and square design among major and micronutrients (X1-X5). such as A1, A2, A3, A4 and A5, and five concentrations of micronutrients stock solutions such as B1, B2, B3, B4 and B5, and groups (X1-X5) for square design among major nutrients and micronutrients.

Results of cultivating *Haematococcus* sp. KAU-01 in the media combinations described by Table 4C are shown by FIGS. 13A-13E. FIG. 13F shows the superior dry biomass produced by culturing *Haematococcus* sp. KAU-01 in combination A3B3 (AAHKAU) medium in comparison to several conventional culture media.

TABLE 4A

| | Major Nutrients Group | | | | |
| --- | --- | --- | --- | --- | --- |
| | A | B | C | D | E |
| | A1 | A2 | A3 | A4 | A5 |
| Chemicals name | mg/L | mg/L | mg/L | mg/L | mg/L |
| $NaNO_3$ | 187.5 | 281.25 | 375.00 | 468.75 | 562.5 |
| $KNO_3$ | 37.5 | 56.25 | 75.00 | 93.75 | 112.5 |

TABLE 4A-continued

Major Nutrients Group

| Chemicals name | A<br>A1<br>mg/L | B<br>A2<br>mg/L | C<br>A3<br>mg/L | D<br>A4<br>mg/L | E<br>A5<br>mg/L |
|---|---|---|---|---|---|
| $Ca(NO_3)_2$ | 12.50 | 18..75 | 25.00 | 31.25 | 37.50 |
| $Mg(NO_3)_2 \cdot 6H_2O$ | 27.50 | 41.25 | 55.00 | 68.75 | 82.50 |
| $K_2HPO_4$ | 22.50 | 33.75 | 45.00 | 56.25 | 67.5 |
| $KH_2PO_4$ | 20.00 | 30.00 | 40.00 | 50.00 | 60.00 |
| $K_2SO_4$ | 5.00 | 7.50 | 10.00 | 12.50 | 15.00 |
| $MgSO_4 \cdot 7H_2O$ | 11.88 | 17.81 | 23.75 | 26.69 | 35.63 |
| Urea | 0.88 | 1.31 | 1.75 | 2.19 | 2.63 |
| $HNO_3$ | 32.50 µl | 48.75 µl | 65.00 µl | 81.25 µl | 97.50 µl |
| $H_3PO_4$ | 7.50 µl | 11.25 µl | 15.00 µl | 18.75 µl | 22.50 µl |

TABLE 4B

Micronutrients Group

| Chemicals name | B1<br>mg/L | B2<br>mg/L | B3<br>mg/L | B4<br>mg/L | B5<br>mg/L |
|---|---|---|---|---|---|
| $FeCl_3 \cdot 6H_2O$ | 1.75 | 2.63 | 3.50 | 4.38 | 5.25 |
| $H_3BO_3$ | 0.50 | 0.75 | 1.00 | 1.25 | 1.50 |
| $Co(NO_3)_2 \cdot 6H_2O$ | 0.13 | 0.19 | 0.25 | 0.31 | 0.38 |
| $K_2Cr_2O_7$ | 0.05 | 0.08 | 0.10 | 0.13 | 0.15 |
| $CuSO_4 \cdot 5H_2O$ | 0.05 | 0.08 | 0.10 | 0.13 | 0.15 |
| $MnSO_4 \cdot H_2O$ | 0.13 | 0.19 | 0.25 | 0.31 | 0.38 |
| $ZnSO_4 \cdot 6H_2O$ | 0.38 | 0.56 | 0.75 | 0.94 | 1.13 |
| $(NH_4)_6Mo_7O_{24} \cdot 4H_2O$ | 0.13 | 0.19 | 0.25 | 0.31 | 0.38 |
| $Na_2$-ETDA | 0.50 | 0.75 | 1.00 | 1.25 | 1.50 |
| HCl | 0.500 µl | 0.750 µl | 1.00 µl | 1.25 µl | 1.50 µl |

TABLE 4C

Design combinations

| X1 | X2 | X3 | X4 | X5 |
|---|---|---|---|---|
| A1 B1 | A2B1 | A3B1 | A4B1 | A5B1 |
| A1 B2 | A2B2 | A3B2 | A4B2 | A5B2 |
| A1 B3 | A2B3 | A3B3 | A4B3 | A5B3 |
| A1 B4 | A2B4 | A3B4 | A4B4 | A5B4 |
| A1 B5 | A2B5 | A3B5 | A4B5 | A5B5 |

This advantageous formulation described by Table 1 ("A3B3" formulation described by Tables 4A and 4B) was designated Affan-Adnan Haematococcus King Abdulaziz University or "AAHKAU" culture medium. The concentrations of elemental Ca and Mg are 4.83 and 6.46 milligram per liter in the AAHKAU medium formulation. These may be slightly higher when water containing Ca and Mg is used to produce the medium. Preferably, the above concentrations of Ca and Mg do not vary by more than ±1, 2, 3, 4, 5, 10, 15 or 20% in modified forms of AAHKAU medium and preferably, any added Ca and Mg is added as a nitrate salt.

To avoid or minimize turbidity and enhance growth of Haematococcus the inventors found that it was important to keep the concentration of Ca (elemental) and Mg (elemental) from all ingredients in AAHKAU medium or its derivatives between 2, 2.5, 3, 3.5, 4, 4.5, 5, 5.5, 6.0, 6.5, 7, 7.5, and 8 for ionic/elemental Ca and between 2, 2.5, 3, 3.5, 4, 4.5, 5, 5.5, 6, 6.5, 7, 7.5, 8, 8.6, 9, 9.5, and 10 for ionic/elemental Mg.

Preferably the minimum and maximum concentrations of elemental calcium range from 2.41 to 7.24 mg/L (or any intermediate value within this range) and those of elemental Mg range from 3.23 and 9.69 mg/L (or any intermediate value within this range) and concentrations of Ca ion more than 7.24 and Mg ion more than 9.69 are not used to avoid substantial cell lysis and turbidity. Most preferably for superior growth without cell lysis and turbidity concentrations of about 4.83 and 6.46 mg/L of calcium and magnesium, respectively, are used.

Alternative formulations of AAHKAU medium may be used to culture Haematococcus include modified AAHKAU medium produced by other combinations of A1-A5×B1-B5 (see Table 4C, for example) or produced by varying the concentration of one or more ingredients in formulations A3 or B3 by 1, 2, 3, 4, 5, 6, 7, 8, 9, 10, 15, 20, 25, 30, 35, 40, 45 or 50%. Affan-Adnan-Haematococcus-King Abdulaziz University (AAHKAU).

$3^{rd}$ step of culture. After formulation of the medium, Haematococcus sp. KAU-01 was grown in AAHKAU medium and other reported media (OHM, RM, Basal and HK media) to compare the growth performance. For growth study in AAHKAU medium, two types of water were used, one was distilled water which was name as AAHKAU-land another was tap water from the municipal water supply which was named as AAHKAU-2. Both of AAHKAU-1 and AAHKAU-2 were kept 4 hours after adding of stock solutions of AAHKAU culture medium at low pH (2.88), since stock solution-A and B were highly acidic (pH 0.18). The pH was then adjusted to 7.00 by adding $Na_2CO_3$. The culture was done in two liter Erlenmeyer flasks containing 1000 mL of each culture medium. The culture comparisons were conducted at same light intensity and temperature with L:D cycle of 12:12 hr. Gentle aeration was provided continuously provided to agitate the culture.

Microscopic observations. Morphological characteristics of the isolated microalga were investigated under inverted light microscope (LM) and photographed. LM based analysis was done from the mono species isolated Haematococcus sp. KAU-01 microalga.

Vegetative motile cell with two flagella, semitransparent trilaminar sheath between cytoplasm, cytoplasmic strands that attaches the main cell body to the theca or the outer cell wall and pyrenoids were observed under inverted light microscope (FIG. 9). The shapes of biflagellate vegetative cells were ovoid to ellipsoidal averaging 27.7±3.3 µm in length and 22.0±4.2 µm in diameter (FIG. 10A).

During the laboratory culture, the flagellated cells were changed to immotile intermediate cells which ere palmelloid with some astaxanthin accumulation; see FIGS. 10A and 10B. Within 2-3 days the cells turned into red cysts cells or aplanospores; FIG. 10C. An average diameter of both immotile with central red and green toward periphery or red spherical palmelloid cells were 35.6±8.2 µm. The average diameter of the relatively large red cyst cells diameter was above 65 µm; FIGS. 10B and 10C.

The red cyst started asexual reproduction after 2 days of inoculation into new culture medium (FIG. 10D and FIG. 10E) then the daughter cells came out by breaking cell wall (FIG. 10F). Cells of the palmelloid stage reproduced asexually by cell division and formed 4 to 64 zoospores (FIG. 10D and FIG. 10E).

In other culture media, lysed cells were seen and sometimes whole cultured cells or some of culture was found to be lysed without forming cyst. Lysis could be stopped by gradually increasing the concentration of $Ca(NO_3)_2$ up to 25.00 $mgL^{-1}$. This concentration was considered as the primary concentration for making Haematococcus sp. KAU-01 culture medium. In some embodiments, the concentration of this anhydrous ingredient or an equivalent molar amount of a hydrate of $Ca(NO_3)_2$ will range from at least 12.50, 18.75, 25.00, 31.25, 37.50 mg/L. In some embodiments, a combined concentration of Ca ions from $Ca(NO_3)_2$ or a hydrate thereof will range from ±25, 20, 15, 10, 5, 2.5, or 1% of the total Mg ion concentration of AAHKAU medium as described in Table 1.

The fate of cells cultured without addition of $Ca(NO_3)_2$ is shown in FIGS. 11A-11D.

In some other embodiments, a concentration of $Mg(NO_3)_2 \cdot 6H_2O$ (or an equivalent molar amount of anhydrous $Mg(NO_3)_2$ will range from at least 40, 45, 50, 55, 60, 65, 70, 75, 80, 85, 90, 100, 110 or 120 ml/L.

Figure 12A:
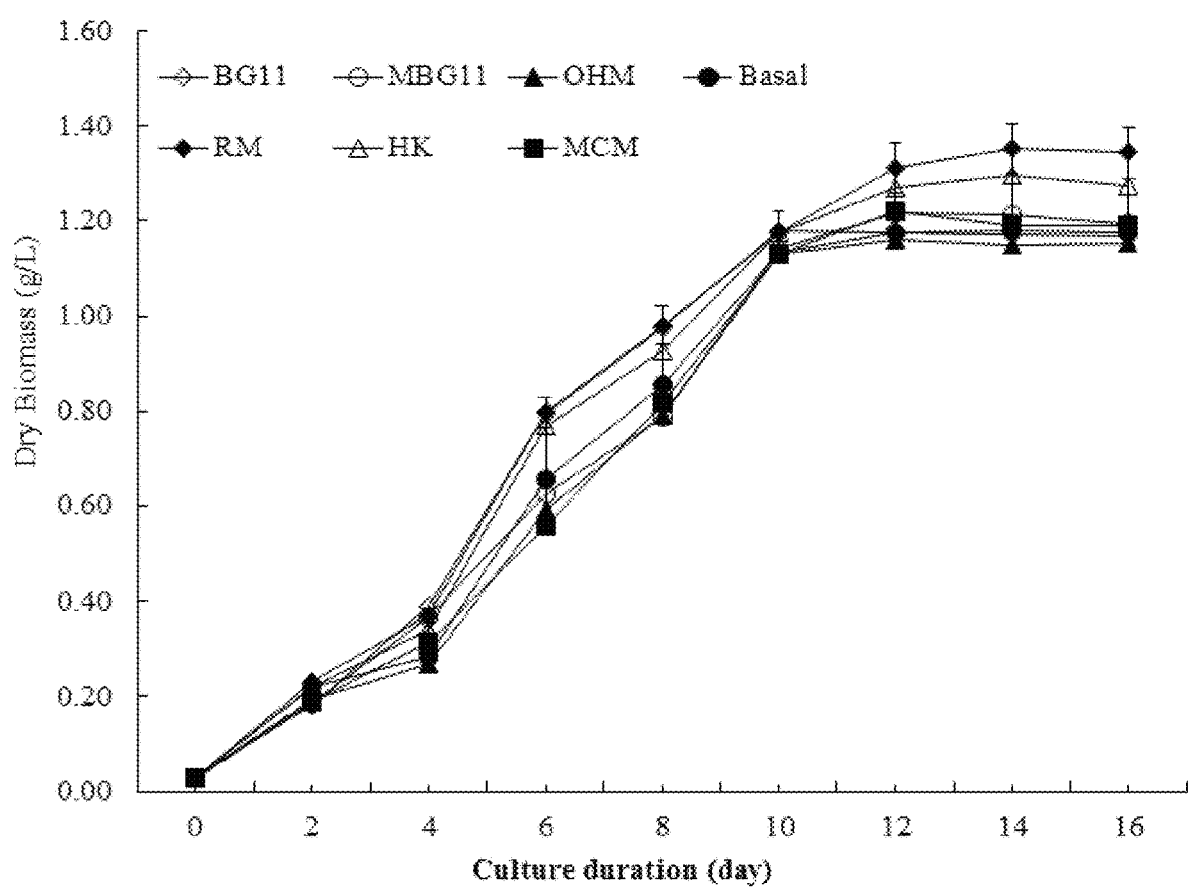
FIG. 12A. Growth performance and biomass (dry wt. $gL^{-1}$) production of *Haematococcus* sp. KAU-01 grown in seven different culture media as comparable to AAHKAU medium.

Growth and biomass production in different culture media in $1^{st}$ step of culture. The dry biomass production $(g/L^{-1})$ differed depending on the selected culture media. Moreover, peak growth in view of biomass production occurred at different times or different days depending on the culture medium selection. In BG11 culture medium, the highest biomass production was 1.18 $gL^{-1}$ on $10^{th}$ day of culture. Similarly, in MCM, MBG11 or OHM culture medium the highest biomass production, respectively, 1.22, 1.22 and 1.16 $gL^{-1}$ on $12^{th}$ day of culture. Biomass production in Basal, HK and RM culture media were 1.18, 1.29 and 1.35 $gL^{-1}$ on $14^{th}$ day of culture (FIG. 12A). However, the highest biomass production was in RM culture medium, followed by HK and Basal media (FIG. 12A).

Figure 12B:
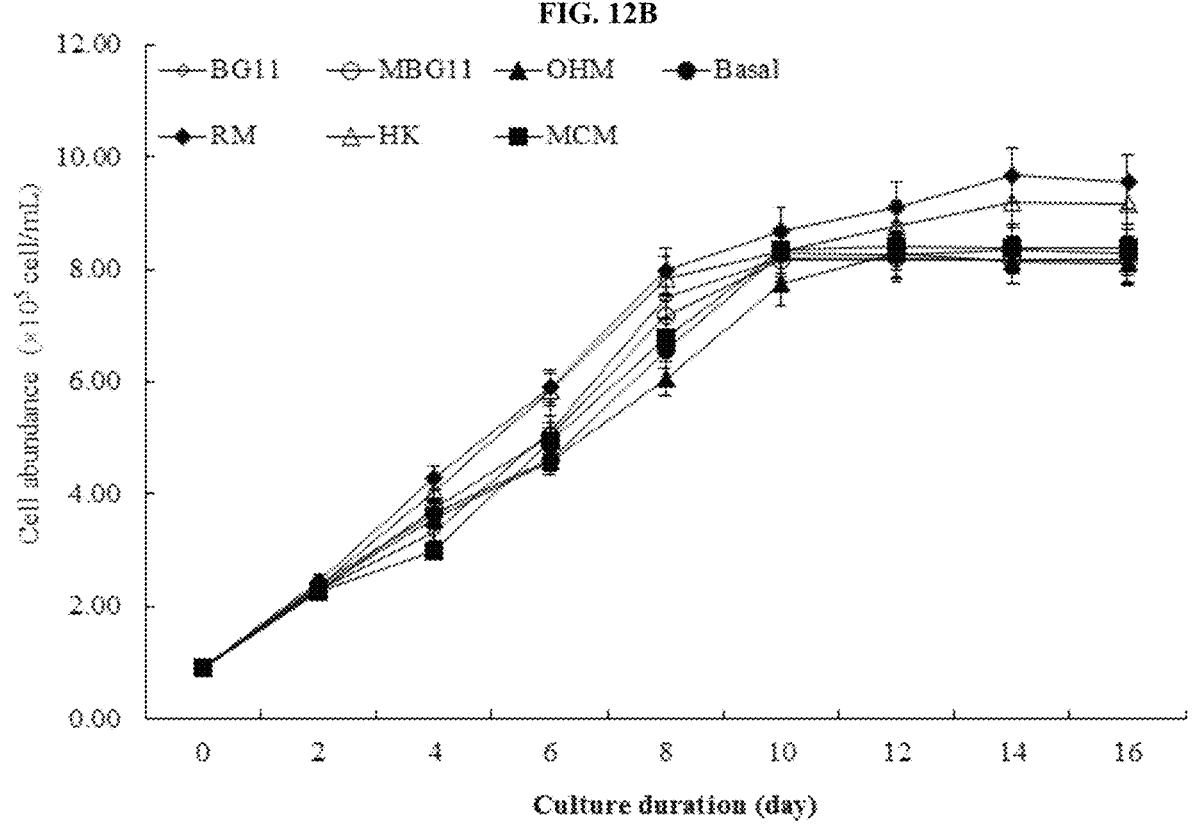
FIG. 12B. Growth performance and cell abundance of *Haematococcus* sp. KAU-01 grown in seven different culture media as comparable to AAHKAU medium.

The result of cell abundance Haematococcus sp. KAU-01 also showed similar growth pattern as it was found in dry biomass estimation. In BG11 culture medium the highest cell abundance was $8.19 \times 10^5$ cells $L^{-1}$ on $10^{th}$ day of culture. Similarly, in MBG11, OHM and MCM culture media, the maximum cell abundance respectively was $8.19 \times 10^5$, $8.27 \times 10^5$ and $8.40 \times 10^5$ cells $L^{-1}$ on $12^{th}$ day of culture. However, the highest cell abundance among the culture was $9.67 \times 10^5$ cells $L^{-1}$ in RM culture medium, followed by HK ($9.20 \times 10^5$) and basal ($8.34 \times 10^5$) culture media on $14^{th}$ day of culture (FIG. 12B). Growth of Haematococcus sp. KAU-01 in AAHKAU culture medium in the $2^{nd}$ step of culture. Haematococcus sp. KAU grew well in all square combinations of 'A and B stock solutions mixed culture media. The higher biomass production was in major nutrient C group (media combinations A3B1; A3B2; A3B3; A3B4; A3B5) than those of A, B, D and E groups. In C group, the biomass production was 1.86 $gL^{-1}$ in A3B3, followed by A3B4 and A3B5 (FIGS. 13A, 13B, 13C, 13D and 13E). Therefore, AAHKAU (A3B3) culture medium recipe was considered to be the most advantageous medium for growth of Haematococcus sp. KAU-01 and designated AAHKAU medium.

Figure 14A:
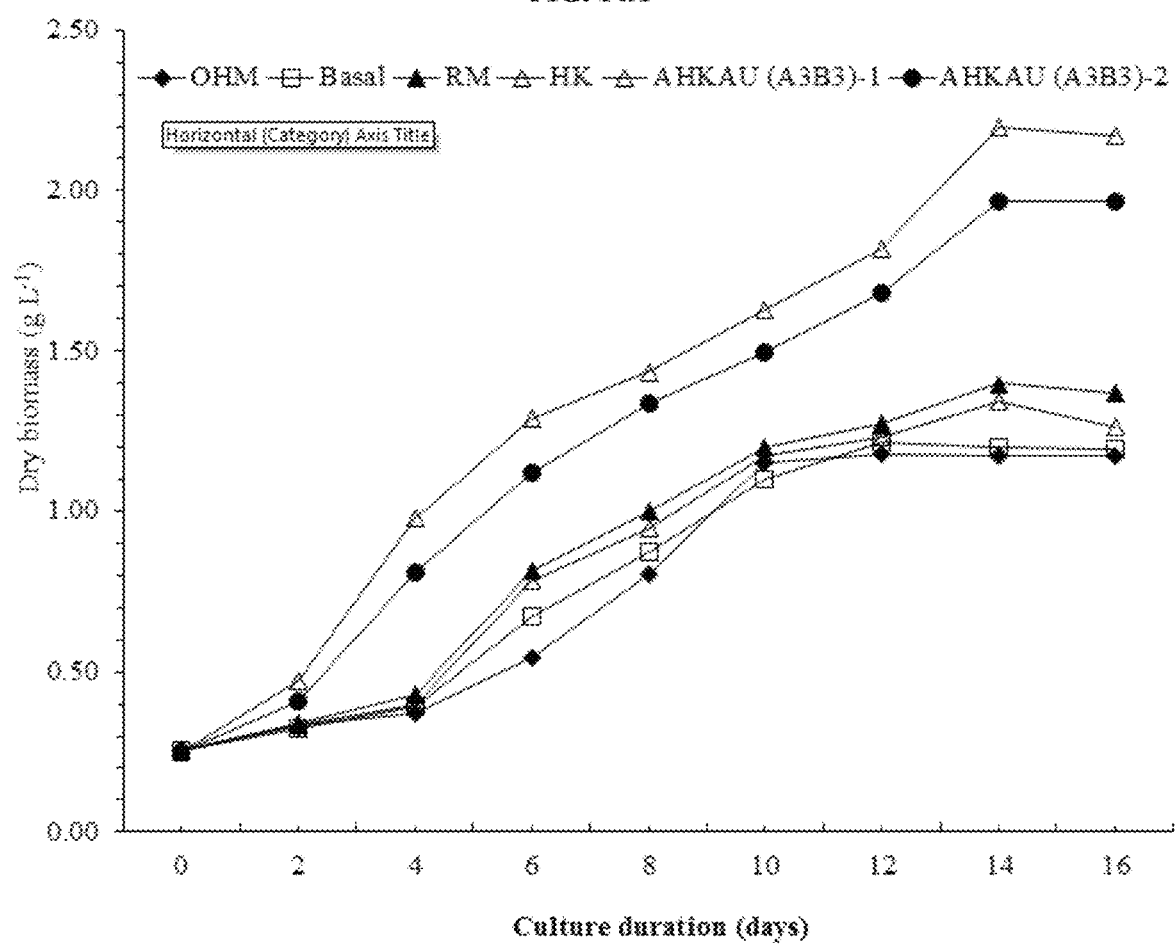
FIG. 14A. Variation of biomass production of *Haematococcus* sp. KAU-01 grown in comparative culture media OHM, Basal, RM, HK and AAHKAU (A3B3) 1 (sterile filtered, distilled water) and AAHKAU (A3B3) 2 (non-sterile tap water). AAHKAU-1 was prepared autoclaved sterile distilled water and AAHKAU-2 was prepared using municipal supplied water which has been not been directly acid treated, but which was made acidic after dilution of stock solution of 'A' and 'B' as both solution contain acids.

For the final step of culture in selected AAHKAU and reported media a Haematococcus sp. KAU-01 growth experiment was conducted to compare the growth and biomass production with other conventional media. Haematococcus sp. KAU-01 was grown in OHM, Basal, RM, HK and AAHKAU (A3B3) culture media. The biomass production was highest 2.20 $gL^{-1}$ in AAHKAU medium, followed by RM (1.37 $gL^{-1}$) and HK (1.31 $gL^{-1}$), respectively (FIG. 14A). Maximum specific growth ($\mu_{max}$ $d^{-1}$) rate was 0.161 and 0.163 $d^{-1}$ on $12^{th}$ day of culture in basal and OHM culture media.

Figure 14B:
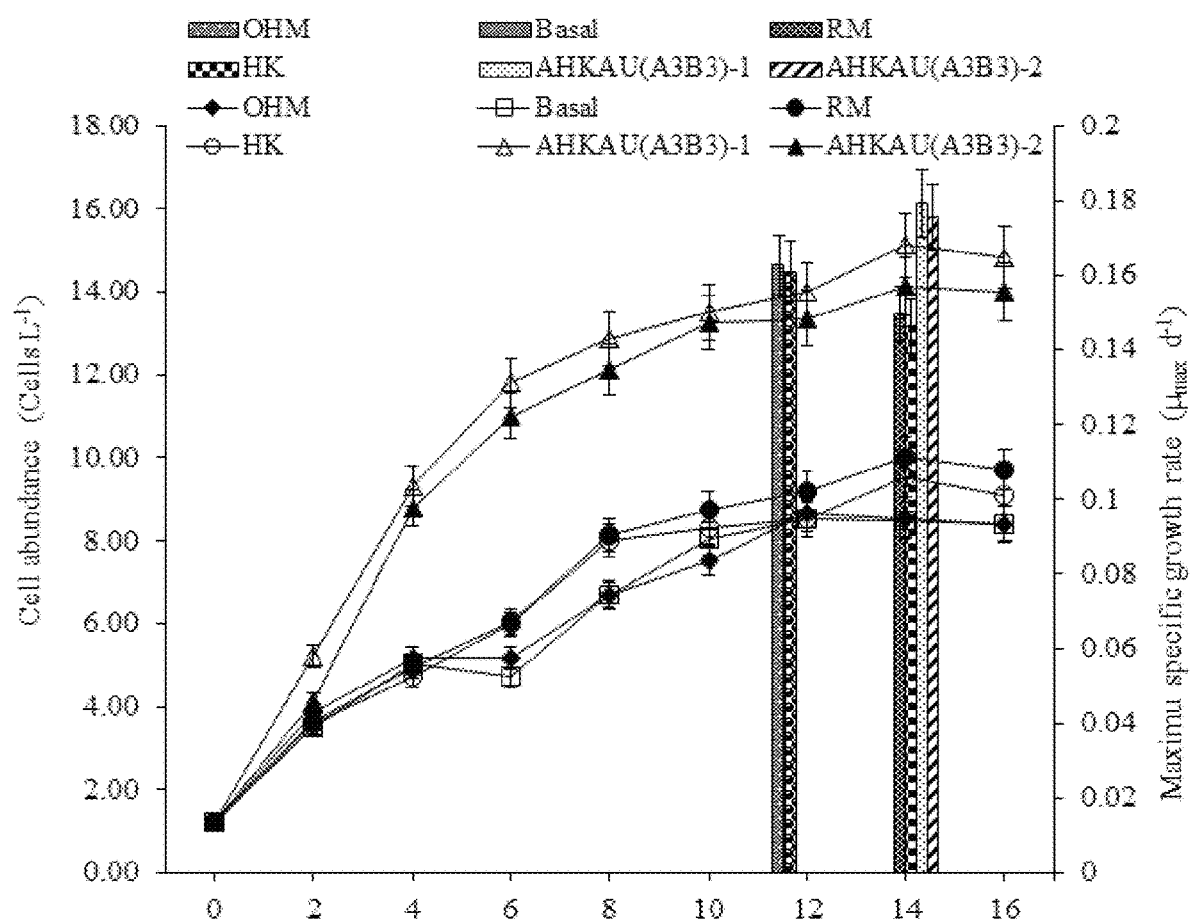
FIG. 14B. Variation in maximum specific growth rate ($u_{max}d^{-1}$) and growth curve with cell abundance (Cells $L^{-1}$) of *Haematococcus* sp. KAU-01 cultured in different culture media including newly prepared AAHKAU (A3B3) medium.

The highest the $\mu$max $d^{-1}$ was 0.179 $d^{-1}$ on $14^{th}$ day of culture in AAHKAU-1, followed by 0.150 and 0.146 $d^{-1}$ in RM and HK media, respectively on same day of culture. In case of AAHKAU-2, the biomass production, cell abundance and $\mu_{max}$ $d^{-1}$ were 1.96 $gL^{-1}$, $14.13 \times 10^5$ cells $L^{-1}$ and 0.174 $d^{-1}$, respectively (FIG. 14B).

Morphological features of Haematococcus sp. KAU-01 are illustrated in FIG. 9. The motile cell having several pyrenoids, two flagella and cytoplasmic strands connecting with main cell body and outer cell wall were observed under inverted light microscope. The motile flagellated cell typically exhibits a voluminous, transparent and gelatinous looking cell wall which is the characteristic of Volvocalean motile cells. Haematococcus sp. are characterized by ovoid, ellipsoid or spherical cells and 34-37.5 μm in diameter (up to 5 μm broad and 63 μm long). The cell wall is widely separated from the protoplast without a papilla, protoplast with a beak-like apex not reaching up to the wall, plasma strands branched and connected with cell wall, chloroplast with thick membrane having 6-8 (up to 15) scattered pyrenoids. These microscopic characteristics are similar to motile cells of Haematococcus sp. KAU-01.

During the laboratory culture, the flagellated cells converted to immotile intermediate cells (palmelloid with some astaxanthin accumulation). Those cells were picked up following MSM technique and kept into multiwall tissue culture plate with distilled water under same light condition as culture. After 3 days all intermediate cells turn into deep red cyst. The red cysts again inoculated into fresh media and observed after certain interval for changing to different stage of life cycle. There were 4 to 64 daughter cells were observed in the red cyst and after few hours the daughter cells ruptured the cell wall of the cyst and motile cells came out and start to multiply. A similar observation was made by Hagen et al. (2001) who indicated that the developmental cycle of Haematococcus pluvialis, flagellates are formed by germination of resting cells after getting favorable environmental condition. Consequently, the inventors place their isolate within the genus Haematococcus sp. based on light microscopic study of motile cells and life cycle of this alga. This new isolate and species within this genus was designated Haematococcus sp. KAU-01.

During culture of Haematococcus sp. KAU-01, the broken or lysed cells were observed in the culture medium prepared without or with low concentrations of calcium salts. The cell wall of Haematococcus sp. KAU-01 was not broken or ruptured when $Ca(NO)_3$ concentrations ranged from 12.50 to 37.50 $mgL^{-1}$ in culture medium where 25.00 $mgL^{-1}$ of $Ca(NO)_3$ gave the best result for growth. A higher concentration was found to stop the movement of flagellated motile cells and inducing to form cyst. The inventors observed that Haematococcus sp. KAU-01 grew between pH 5.65 and 9.80 without significant lysis or rupture of cells or formation of cysts. They also found that a suitable concentration of calcium protected Haematococcus from lysis at least until the pH of the culture medium exceeds 9.8. This inhibition of cell lysis enhanced biomass yield. Additionally, calcium nitrate salts were used rather than calcium chloride or calcium phosphate. During photosynthesis chloride ions play a role in balancing of potassium and in water splitting however, nitrate plays an important role as a major plant nutrient. Calcium phosphate makes the culture medium milky turbid when adjusted to pH 7.5. The nitrate supplied by calcium nitrate also plays a role in biosynthesis of amino acids and for total protein and carbohydrate production of cells.

Growth and biomass production in different culture media. The growth rate and biomass production of Haematococcus sp were influenced by several physical and chemical factors. Chemical factors include selection of proper combinations of macro and micronutrients and physical factors include culture temperature and illumination. The inventors found that Haematococcus sp. KAU-01 showed similar growth as H. pluvialis when Haematococcus sp. KAU-01 was cultured under at light intensity of 120 μE $m^{-2}$ $s^{-1}$ on a 12:12 L:D photo cycle. However, surprising results were obtained when Haematococcus sp. KAU-01 was grown in AAHKAU medium and other reported media at 100 µE m$^{-2}$ s$^{-1}$ on a 12:12 h L:D photo cycle. The cell abundance and biomass production were higher in light intensity of 100 µE m$^{-2}$ s$^{-1}$ than that of 120 µE m$^{-2}$ s$^{-1}$ under same L:D photo cycle intensity in all culture media.

Among the all culture, the highest cell abundance, µmaxd$^{-1}$ and biomass production were in AAHKAU culture medium. RM, BG11 and Basal media are more often used for growing *H. pluvialis*. Among those media, RM and basal media showed the higher cell abundance which was 9.50× 10$^5$ and 8.85×10$^5$ cells mL$^{-1}$, and the maximum specific growth rate was 0.195 and 0.177 d$^{-1}$, respectively. The remarkable growth, cell abundance and biomass production achieved in AAHKAU medium exceeded that of any other reported culture media. While not being bound to any theory or explanation, the inventors believe that the Ca$^{2+}$, Mg$^{2+}$, and NO$_3$-content of AAHKAU medium in combination with large amount of iron may protect against cell wall lysis, increase chlorophyll content and protein synthesis and ultimately enhance growth and biomass production.

To test the effects of culturing *Haematococcus* in tap water a comparative AAHKAU-2 culture was performed using water to observe the growth and biomass production by eradication of contaminant species by adding of acidic stock solution of AAHKAU. In AAHKAU-2 culture, *Haematococcus* sp. KAU-01 grew well in comparison with reported media and there were no more contaminant species found. In tap water some microalgae (*Scenedesmus* sp. *Chlamydomonas* sp., etc.) was found to grow after enriched with F/2 culture medium nutrients during trial error study of growth of *Haematococcus* sp. KAU-01. It was also observed that growth of *Haematococcus* sp. KAU was stopped in presence of contaminating microalgae, for example, *Haematococcus* sp. KAU-01 was lost from a culture containing *Scenedesmus* sp. KAU-01. Biomass production was lower in AAHKAU-2 (tap water) than that the biomass production of AAHKAU-1.

In Jeddah, tap water for domestic use is supplied from desalination plants for domestic use. The desalinated water contains 100-1000 mgL$^{-1}$ of total dissolved solids, and the concentration of calcium is almost 200 mgL$^{-1}$ of water; Hussein, M. & Magram, S. F., *Domestic Water Quality in Jeddah, Saudi Arabia*. JKAU: ENG. SCI. 2012, 23, 207-223. High concentrations of Ca$^{2+}$ might have played role to slow growth of *Haematococcus* sp. KAU-01 as discussed above. It is preferable to use distilled water of soft water with a low calcium content to formulate AAHKAU medium so as to control the calcium and magnesium concentrations in the medium. Preferably, the concentrations of ionic/elemental calcium and magnesium fall within the ranges described by A1-A5 in Table 4A. These are for ionic/elemental calcium 3.05 to 9.16 mg/L and for ionic/elemental Mg 3.78 to 11.34 mg/L. Preferably, the concentrations of ionic/elemental Ca and Mg are about 6.11±0.611 mg/L for calcium and 7.56±0.756 mg/L for magnesium which encompass the concentrations in AAHKAU medium. For industrial-scale production water having a low concentration of Ca or soft water will be suitable. Water obtained by desalination may also be used.

This Example shows for the first time the morphological characteristics of *Haematococcus* sp. KAU-01 isolated in the Kingdom of Saudi Arabia and the GCC and formulation of an advantageous culture medium for this strain. The new strain grew in all the reported culture media but attained enhanced growth in batch culture in the newly formulated AAHKAU culture medium (AAHKAU).

Ca salt concentration in AAHKAU medium was confirmed to prevent or resist cell wall lysis.

AAHKAU medium stock solutions used to formulated 1× culture medium also conferred the ability to eradicate microbial contaminants found in water that was not autoclaved such as tap water. Consequently, autoclaving of water or culture medium is not required before inoculation of *Haematococcus* sp. providing a way to perform large scale outdoor culture for industrial scale biomass production in hot or tropical countries by *Haematococcus* sp., especially by *Haematococcus* sp. KAU-01 which was isolated in the hot tropical climate of the Kingdom of Saudi Arabia and GCC.

The media, strains, and methods disclosed herein permit scaled-up or industrial-scale microalga cultivation as well as sequestration of greenhouse and flue gases using the developed AAHKAU medium especially in countries with tropical climates, such as the Kingdom of Saudi Arabia.

Terminology used herein is for the purpose of describing particular embodiments only and is not intended to be limiting of the invention.

Equivalent molar amounts of non-hydrated salts may be used in place of the corresponding hydrated salt or compound.

Terms such as "optimized" or "optimize" as used herein include values or characteristics realized by careful selection of features of chimeric DNA constructs or other critical process variables and do not imply use of a known results-effective variable.

As used herein, the singular forms "a", "an" and "the" are intended to include the plural forms as well, unless the context clearly indicates otherwise.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears. The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for producing biomass, comprising:
   culturing *Haematococcus* in a culture medium in the presence of at least one combustion gas and light, thereby producing biomass;
   wherein said culture medium comprises from:
   187.50 to 562.50 mg/L $NaNO_3$, 37.50 to 112.50 mg/L $KNO_3$, 12.50 to 37.50 mg/L $Ca(NO_3)_2$, 27.50 to 82.50 mg/L $Mg(NO_3)_2 \cdot 6H_2O$, 22.50 to 67.50 mg/L $K_2HPO_4$, 20.00 to 60.00 mg/L $KH_2PO_4$, 5.00 to 15.00 mg/L $K_2SO_4$, 11.88 to 35.63 mg/L $MgSO_4 \cdot 7H_2O$, 0.88 to 2.63 mg/L urea, 32.50 to 97.50 µl/L $HNO_3$, 7.50 to 22.50 µl/L in $H_3PO_4$, and water; wherein said culturing comprises removing eicosapentaenoic acid (EPA) from the culture medium while retaining viable *Haematococcus*.

2. The method of claim 1, wherein the culture medium further comprises 1.75 to 5.25 mg/L $FeCl_3 \cdot 6H_2O$, 0.50 to 1.50 mg/L $H_3BO_3$, 0.13 to 0.38 mg/L $Co(NO_3)_2 \cdot 6H_2O$, 0.05 to 0.15 mg/L $K_2Cr_2O_7$, 0.05 to 0.15 mg/L $CuSO_4 \cdot 5H_2O$, 0.13 to 0.38 mg/L $MnSO_4 \cdot H_2O$, 0.38 to 1.13 mg/L $ZnSO_4 \cdot 6H_2O$, 0.13 to 0.38 mg/L $(NH_4)_6Mo_7O_{24} \cdot 4H_2O$, 0.5 to 1.5 mg/L $Na_e$-EDTA, and 0.500 to 1.50 µl/L HCl.

3. The method of claim 1, wherein the culture medium further comprises 1.75 to 5.25 mg/L $FeCl_3 \cdot 6H_2O$, 0.50 to 1.50 mg/L $H_3BO_3$, 0.13 to 0.38 mg/L $Co(NO_3)_2 \cdot 6H_2O$, 0.05 to 0.15 mg/L $K_2Cr_2O_7$, 0.05 to 0.15 mg/L $CuSO_4 \cdot 5H_2O$, 0.13 to 0.38 mg/L $MnSO_4 \cdot H_2O$, 0.38 to 1.13 mg/L $ZnSO_4 \cdot 6H_2O$, 0.13 to 0.38 mg/L $(NH_4)_6Mo_7O_{24} \cdot 4H_2O$, 0.5 to 1.5 mg/L $Na_e$-EDTA, and 0.500 to 0.150 µl/L HCl; and further comprises 0.8 to 1.2 mg/L thiamine, 0.0024 to 0.0036 mg/L+D-biotin, and 0.0008 to 0.0012 mg/L cyanocobalamin.

4. The method of claim 1, wherein the culture medium is prepared using water that has had its pH lowered to pH 3.5 or below and then raised to at least pH 6.5 prior to inoculation of the culture medium with *Haematococcus*.

5. The method of claim 1, wherein the water in the culture medium comprises natural seawater.

6. The method of claim 1, wherein the culture medium further comprises or is contacted with exogenous carbon dioxide.

7. The method of claim 1, wherein the culture medium further comprises or is contacted with at least 5 to 25 vol % exogenous $CO_2$.

8. The method of claim 1, wherein the culture medium further comprises or is contacted with at least one of carbon monoxide, Nox or Sox.

9. The method of claim 1, wherein the culture medium further comprises or is contacted with at least one gas obtained from combustion of coal.

10. The method of claim 1, wherein said culturing comprises removing cell debris from the culture medium while retaining viable *Haematococcus*.

11. The method of claim 1, wherein said culturing comprises replacing at least 5% of spent culture medium with fresh culture medium and adjusting the pH of the culture medium to range from pH 6 to 8.

12. The method of claim 1, wherein the *Haematococcus* has 18s or ITS2rDNA that is at least 98% 100% identical to the 18s or ITS2 rDNA of *Haematococcus* sp. KAU-01.

13. The method of claim 1, wherein the *Haematococcus* is *Haematococcus* sp. KAU-01 or a subculture thereof.

14. The method of claim 1, wherein the *Haematococcus* is *Haematococcus* sp. KAU-01.

15. The method of claim 1, further comprising recovering astaxanthin or another carotenoid from biomass produced by the *Haematococcus*.

* * * * *